(12) United States Patent
Edens et al.

(10) Patent No.: US 8,524,225 B2
(45) Date of Patent: Sep. 3, 2013

(54) USE OF PROLINE SPECIFIC ENDOPROTEASES TO HYDROLYSE PEPTIDES AND PROTEINS

(75) Inventors: Luppo Edens, Rotterdam (NL); Melissa Harvey, Stanwell park (AU); Robertus Antonius Mijndert Van Der Hoeven, Katwijk (NL); Andre Leonardus De Roos, Delft (NL)

(73) Assignee: DSM IP Assets B.V., Te Heerlen (NL)

( * ) Notice: Subject to any disclaimer, the term of this patent is extended or adjusted under 35 U.S.C. 154(b) by 1420 days.

(21) Appl. No.: 10/572,811

(22) PCT Filed: Sep. 23, 2004

(86) PCT No.: PCT/EP2004/010782
§ 371 (c)(1),
(2), (4) Date: Mar. 22, 2006

(87) PCT Pub. No.: WO2005/027953
PCT Pub. Date: Mar. 31, 2005

(65) Prior Publication Data
US 2007/0031399 A1      Feb. 8, 2007

(30) Foreign Application Priority Data

Sep. 23, 2003  (EP) .................................... 03078012
Nov. 6, 2003   (EP) .................................... 03078496

(51) Int. Cl.
*A61K 38/48*       (2006.01)
(52) U.S. Cl.
USPC ....................................................... 424/94.63
(58) Field of Classification Search
None
See application file for complete search history.

(56) References Cited

U.S. PATENT DOCUMENTS

| | | |
|---|---|---|
| 2004/0067279 A1 | 4/2004 | Delest et al. |
| 2004/0115306 A1 | 6/2004 | Lopez et al. |
| 2004/0241664 A1 | 12/2004 | Dekker et al. |
| 2004/0241791 A1 | 12/2004 | Edens et al. |
| 2005/0064403 A1 | 3/2005 | Edens et al. |
| 2005/0175622 A1 | 8/2005 | Edens et al. |
| 2005/0256057 A1 | 11/2005 | Edens et al. |
| 2005/0271744 A1 | 12/2005 | van der Heyden et al. |
| 2006/0257544 A1 | 11/2006 | Edens et al. |
| 2007/0207944 A1 | 9/2007 | Edens et al. |
| 2008/0113896 A1 | 5/2008 | Edens et al. |

FOREIGN PATENT DOCUMENTS

| | | |
|---|---|---|
| DD | 262 999 A1 | 12/1988 |
| DE | 262 999 | 12/1988 |
| EP | 1 224 869 B1 | 9/2004 |
| EP | 0 967 285 B1 | 9/2007 |
| GB | 1 490 723 | 11/1977 |
| WO | WO 01/24816 | 4/2001 |
| WO | WO 02/45523 | 6/2002 |
| WO | WO 02/45524 A2 | 6/2002 |
| WO | WO 02/46381 A2 | 6/2002 |
| WO | WO 0245524 A2 * | 6/2002 |
| WO | WO 03/028745 | 4/2003 |
| WO | WO 03/068170 | 8/2003 |

OTHER PUBLICATIONS

Hausch F. et al. Intestinal Digestive Resistance of Immunodominant Gliadin Peptides, Am. J. Physiol. Gastrointest. Liver Physiol., Oct. 2002, vol. 283, pp. G996-G1003, entire document (First publishes on Jun. 5, 2002).*
Frazer "The present state of knowledge on the celiac syndrome" J. Pediatrics 57 (2):262-276 (1960).
Frazer et al. "Gluten-induced enteropathy. The effect of partially digested gluten" Lancet 2 (7097):252-255 (1959).
Krainick et al. "Weitere Untersuchungen über den schädlichen weizenmehleflekt be der cöliakie" Helvetica Paediatrica Acta 14 (2):124-140 (1959).
Kleinbaum et al. "Neue gesichtspunkte füf eine diätetische beeinflussung der zöliakie" Internationalen Tagung zu Problemen der Getreideverarbeitung und Getreidechemie 7:75-83 (1975).
Messer et al. "Oral papain in gluten intolerance" Lancet 2 (7993):1022 (1976).
Messer et al. "Studies on the mechanism of destruction of the toxic action of wheat gluten in coeliac disease by crude papain" Gut 5:295-303 (1964).
Piper et al, "Effect of prolyo endopeptidase on digestive-resistant gliadin peptides in Vivo", Journal of Pharmacology and Experimental Therapeutics, vol. 311, No. 1, Oct. 2004, pp. 213-219.
Marti et al, "Prolyl endopeptidase-mediated destruction of T cell epitopes in whole gluten: chemical and immunological characterization", The Journal of Pharmacology and Experimental Therapeutics, Jan. 2005, vol. 312, No. 1, Jan. 2005.
International Search Report, mailed on Dec. 4, 2005.
Di Cagno et al; "Proteolysis by Sourdough Lactic Acid Bacteria: Effects on Wheat Flour Protein Fractions and Gliadin Peptides Involved in Human Cereal Intolerance"; *Appl. Environ. Microbiol.*, vol. 68, pp. 623-633 (2002).
Simpson, D.; "Proteolytic degradation of cereal prolamins-the problem with proline"; *Plant Science*, vol. 161, pp. 825-838 (2001).
Experimental Evidence; Memo, DSM; "Application of proline specific protease in mashing"; 2 pgs. (2012).
Lee, M.S., et al; "LC/MS Applications in Drug Development"; *Mass Spectrometry Reviews*, vol. 18, pp. 187-279 (1999).
Lu Shan et al; "Structural Basis for Gluten Intolerance in Celiac Sprue"; *Science*, vol. 297, p. 2275 (2002).
Hausch, F., et al; "Intestinal digestive resistance of immunodominant gliadin peptides"; *Am. J. Physiol Gastrointest Liver Physiol*; 283:G996-G1003, (2002).

(Continued)

*Primary Examiner* — Jon P Weber
*Assistant Examiner* — Satyendra Singh
(74) *Attorney, Agent, or Firm* — Nixon & Vanderhye

(57) ABSTRACT

The present invention relates to a process for the proteolytic hydrolysis of a peptide or a polypeptide, said peptide or polypeptide comprising 4 to 40, preferably 5 to 35, amino acid residues and said peptide or polypeptide is not hydrolysable by subtilisin whereby said peptide or polypeptide is hydrolysed by a proline specific endo protease at a pH of 6.5 or lower, preferably 5.5 or lower and more preferably 5.0 or lower to hydrolyse said peptide or polypeptide.

10 Claims, 3 Drawing Sheets

(56) References Cited

OTHER PUBLICATIONS

EPO Examining Division, Mewburn Ellis LLP; 1 pg. (2010).
Facts and Arguments; Annex 1, Notice of Opposition Against EP1572127 B1, Filing Date Feb. 14, 2003; First Publication Date Aug. 21, 2003 (18 pgs).
Letter to EPO, European Patent No. 1 572 127 B1, Proprietor: The Board of Trustees of the Leland Stanford Junior University; Proprietor's Response to the Notice of Opposition dated Aug. 23, 2012 (26 pgs).
Brief Communication w/Letter from proprietor of the patent, dated Aug. 23, 2012 (1 pg).
Acknowledgement of receipt, Patent No. EP1572127, date of receipt Aug. 23, 2012 (2 pgs).
Pectinase from Aspergillus Niger, var., D30, Prepared at the $55^{th}$ JECFA (2000), published in FNP 52 Add 8 (2000) superseding tentative specifications prepared at the $31^{st}$ JECFA (1987) and published in FNP 38 (1988) and in FNP 52 (1992) (3 pgs).
First Auxiliary Request, EP 1 572 127, Aug. 2012 (3 pgs).
Second Auxiliary Request, EP 1 572 127, Aug. 2012 (3 pgs).
Oral proceedings requested; Patent No. EP1572127, Apr. 13, 2011 (3 pgs).
Midhagen, G., et al; "High Rate of Gastrointestinal Symptoms in Celiac Patients Living on a Gluten-Free Diet: Controlled Study"; *The American Journal of Gastroenterology*; vol. 98, No. 9, pp. 2023-2026 (2003).
Siniscalchi, M., et al; "Fatigue in adult celiac disease"; *Aliment Pharmacol. Ther.*; vol. 22, pp. 489-494 (2005).
Bruce, C., et al; Alimentary tract and pancreas, "Breakdown of gliadin peptides by intestinal brush borders from celiac patients"; *Gut*, vol. 25, pp. 919-924 (1984) D35.
McAdam et al; "Getting to grips with gluten"; *Gut*; vol. 47; pp. 743-745 (2000).
Choe, Y., et al; "Substrate Profiling of Cysteine Proteases Using a Combinatorial Peptide Library Identifies Functionally Unique Specificities"; *Journal of Biological Chemistry*; vol. 281, No. 18 (2006).
Fasano, A.; "Surprises from Celiac Disease"; *Scientific American, Inc.*, pp. 54-61 (2009).
Krainick, H.G., et al; "Further Studies on the Harmful Effects of Wheat Flour in Celiac Disease 2. The effect of the enzymatic degeneration products of gliadin"; *Helvetica Paediatrica Acta*, No. 2, pp. 124-140 (1959) w/English Translation.
Schuppan, D., et al; "Gluten and the Gut-Lessons for Immune Regulation"; *Science*; vol. 29, pp. 2218-2220 (2002).
R&D Directions; vol. 16, No. 3, 5 pgs, (2010).
Source: Elsevier Business Intelligence; Windhover Announces the 2011 "Top Biopharma Projects to Watch"; *Marketwire*; http://www.marketwire.com/printer_friendly?id=1335076; 4 pgs, (Oct. 14, 2010).
Letter to European Patent Office dated Aug. 23, 2012; European Patent No. 1 572 127 B1; Proprietor's Response to the Notice of Opposition; (26 pgs).
Brief Communication w/Letter from the proprietor of the patent dated Jun. 14, 2012 (1 pg).
Grant of Opposition of Time Limit dated Jun. 19, 2012 (1 pg).
Acknowledgement of receipt; EP1572127; Jun. 14, 2012 (1 pg).
Request for extension of time limit EP1572127 dated Jun. 14, 2012 (2 pgs).
Letter to European Patent Office EP 1572127 dated Jun. 14, 2012 (1 pg).
Communication of notices of opposition and request to file observations dated Feb. 17, 2012 (1 pg).
Communication of further notices of opposition dated Feb. 17, 2012 (1 pg).
Communication of a notice of opposition dated Sep. 19, 2012 (1 pg).
Acknowledgement of receipt dated, EP1572127 dated Jan. 13, 2012 (2 pgs).
Memo Re: Application of proline specific protease in mashing; dated Jan. 11, 2012 (2 pgs).
Kleinbaum, H., et al; "Neue Gesichtspunkte für eine diätetische Beeinflussung der Zöliakie"; *International Tagung zu Problemen der Getreideverarbeitung and Getreidechemie*; vol. 7, pp. 75-83 (1975) w/English Translation.
Notice of opposition to a European patent No. EP 1572127, dated Jan. 13, 2012 (10 pgs).
Certified U.S. Appl. No. 60/357,238, filed Feb. 14, 2002 (41 pgs).
Certified U.S. Appl. No. 60/428,033, filed Nov. 20, 2002 (48 pgs).
Certified U.S. Appl. No. 60/380,761, filed May 14, 2002 (68 pgs).
Certified U.S. Appl. No. 60/435,881, filed Dec. 20, 2002 (50 pgs).
Letter to European Patent Office dated May 5, 2010, European Application No. 03711089.7, in reply to Communication of Apr. 28, 2010 (1 pg).
Certified U.S. Appl. No. 60/392,782, filed Jun. 28, 2002 (85 pgs).
Certified U.S. Appl. No. 60/422,933, filed Oct. 2002 (61 pgs).

* cited by examiner

MWM= molecular weight markers

Lanes 1, 3, 5, 7: ovalbumine after 0, 4.75, 20,5 and 27.75 hours of incubation respectively (5µl loaded); lanes 2, 4, 6, 8: 27-mer peptide after 0, 4.75, 20,5 and 27.75 hours of incubation respectively (5µl loaded). Lane 9: 27-mer at 0 hours (2µl loaded).

```
                        SEQUENCE LISTING

<160> NUMBER OF SEQ ID NOS: 58

<210> SEQ ID NO 1
<211> LENGTH: 10
<212> TYPE: PRT
<213> ORGANISM: Artificial
<220> FEATURE:
<221> NAME/KEY: PEPTIDE
<222> LOCATION: (1)..(10)
<223> OTHER INFORMATION: Artificial sequence from plant origin

<400> SEQUENCE: 1

Val Tyr Pro Phe Pro Gly Pro Ile Pro Asn
1               5                   10

<210> SEQ ID NO 2
<211> LENGTH: 4
<212> TYPE: PRT
<213> ORGANISM: Artificial
<220> FEATURE:
<221> NAME/KEY: PEPTIDE
<222> LOCATION: (1)..(4)
<223> OTHER INFORMATION: Artificial sequence from plant origin

<400> SEQUENCE: 2
```

```
Tyr Pro Phe Pro
1

<210> SEQ ID NO 3
<211> LENGTH: 9
<212> TYPE: PRT
<213> ORGANISM: Artificial
<220> FEATURE:
<221> NAME/KEY: PEPTIDE
<222> LOCATION: (1)..(9)
<223> OTHER INFORMATION: Artificial sequence from plant origin

<400> SEQUENCE: 3

Pro Tyr Pro Gln Pro Gln Leu Pro Tyr
1               5

<210> SEQ ID NO 4
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 4

Tyr Pro Gln Pro Gln Leu Pro
1               5

<210> SEQ ID NO 5
<211> LENGTH: 9
<212> TYPE: PRT
<213> ORGANISM: Artificial
<220> FEATURE:
<221> NAME/KEY: PEPTIDE
<222> LOCATION: (1)..(9)
<223> OTHER INFORMATION: Artificial sequence from plant origin

<400> SEQUENCE: 5

Pro Tyr Pro Gln Pro Gln Leu Pro Tyr
1               5

<210> SEQ ID NO 6
<211> LENGTH: 8
<212> TYPE: PRT
<213> ORGANISM: Artificial
<220> FEATURE:
<221> NAME/KEY: PEPTIDE
<222> LOCATION: (1)..(8)
<223> OTHER INFORMATION: Artificial sequence from plant origin

<400> SEQUENCE: 6

Trp Gln Ile Pro Glu Gln Ser Arg
1               5

<210> SEQ ID NO 7
<211> LENGTH: 12
<212> TYPE: PRT
<213> ORGANISM: Artificial
<220> FEATURE:
<221> NAME/KEY: PEPTIDE
<222> LOCATION: (1)..(12)
<223> OTHER INFORMATION: Artificial sequence from plant origin

<400> SEQUENCE: 7

Gln Leu Gln Pro Phe Pro Gln Pro Gln Leu Pro Tyr
1               5                   10

<210> SEQ ID NO 8
```

```
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 8

Gln Pro Phe Pro Gln Pro Gln
1               5

<210> SEQ ID NO 9
<211> LENGTH: 16
<212> TYPE: PRT
<213> ORGANISM: Artificial
<220> FEATURE:
<221> NAME/KEY: PEPTIDE
<222> LOCATION: (1)..(16)
<223> OTHER INFORMATION: Artificial sequence from plant origin

<400> SEQUENCE: 9

Gln Pro Gln Gln Pro Gln Gln Ser Pro Phe Gln Gln Arg Pro Phe
1               5                   10                  15

<210> SEQ ID NO 10
<211> LENGTH: 6
<212> TYPE: PRT
<213> ORGANISM: Artificial
<220> FEATURE:
<221> NAME/KEY: PEPTIDE
<222> LOCATION: (1)..(6)
<223> OTHER INFORMATION: Artificial sequence from plant origin

<400> SEQUENCE: 10

Gln Gln Arg Pro Phe Ile
1               5

<210> SEQ ID NO 11
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 11

Gln Pro Pro Phe Ser Gln Gln Gln Ser Pro Phe Ser Gln
1               5                   10

<210> SEQ ID NO 12
<211> LENGTH: 5
<212> TYPE: PRT
<213> ORGANISM: Artificial
<220> FEATURE:
<221> NAME/KEY: PEPTIDE
<222> LOCATION: (1)..(5)
<223> OTHER INFORMATION: Artificial sequence from plant origin

<400> SEQUENCE: 12

Gln Ser Pro Phe Ser
1               5

<210> SEQ ID NO 13
<211> LENGTH: 6
<212> TYPE: PRT
<213> ORGANISM: Artificial
<220> FEATURE:
<221> NAME/KEY: PEPTIDE
```

```
<222> LOCATION: (1)..(6)
<223> OTHER INFORMATION: Artificial sequence from plant origin

<400> SEQUENCE: 13

Pro Pro Phe Ser Gln Gln
1               5

<210> SEQ ID NO 14
<211> LENGTH: 27
<212> TYPE: PRT
<213> ORGANISM: Artificial
<220> FEATURE:
<221> NAME/KEY: PEPTIDE
<222> LOCATION: (1)..(27)
<223> OTHER INFORMATION: Artificial sequence from plant origin

<400> SEQUENCE: 14

Phe Arg Ala Ser Asp Asn Asp Arg Val Ile Asp Pro Gly Lys Val Glu
1               5                   10                  15

Thr Leu Thr Ile Arg Arg Leu His Ile Pro Arg
            20                  25

<210> SEQ ID NO 15
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 15

Tyr Pro Phe Pro Gly Pro Ile
1               5

<210> SEQ ID NO 16
<211> LENGTH: 4
<212> TYPE: PRT
<213> ORGANISM: Artificial
<220> FEATURE:
<221> NAME/KEY: PEPTIDE
<222> LOCATION: (1)..(4)
<223> OTHER INFORMATION: Artificial sequence from plant origin

<400> SEQUENCE: 16

Tyr Pro Phe Pro
1

<210> SEQ ID NO 17
<211> LENGTH: 5
<212> TYPE: PRT
<213> ORGANISM: Artificial
<220> FEATURE:
<221> NAME/KEY: PEPTIDE
<222> LOCATION: (1)..(5)
<223> OTHER INFORMATION: Artificial sequence from plant origin

<400> SEQUENCE: 17

Tyr Pro Phe Pro Gly
1               5

<210> SEQ ID NO 18
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin
```

```
<400> SEQUENCE: 18

Tyr Pro Phe Pro Gly Pro Ile
1               5

<210> SEQ ID NO 19
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 19

Phe Pro Gly Pro Ile Pro Ser
1               5

<210> SEQ ID NO 20
<211> LENGTH: 8
<212> TYPE: PRT
<213> ORGANISM: Artificial
<220> FEATURE:
<221> NAME/KEY: PEPTIDE
<222> LOCATION: (1)..(8)
<223> OTHER INFORMATION: Artificial sequence from plant origin

<400> SEQUENCE: 20

Tyr Pro Phe Pro Gly Pro Ile Pro
1               5

<210> SEQ ID NO 21
<211> LENGTH: 8
<212> TYPE: PRT
<213> ORGANISM: Artificial
<220> FEATURE:
<221> NAME/KEY: PEPTIDE
<222> LOCATION: (1)..(8)
<223> OTHER INFORMATION: Artificial sequence from plant origin

<400> SEQUENCE: 21

Val Tyr Pro Phe Pro Gly Pro Ile
1               5

<210> SEQ ID NO 22
<211> LENGTH: 9
<212> TYPE: PRT
<213> ORGANISM: Artificial
<220> FEATURE:
<221> NAME/KEY: PEPTIDE
<222> LOCATION: (1)..(9)
<223> OTHER INFORMATION: Artificial sequence from plant origin

<400> SEQUENCE: 22

Val Tyr Pro Phe Pro Gly Pro Ile Pro
1               5

<210> SEQ ID NO 23
<211> LENGTH: 9
<212> TYPE: PRT
<213> ORGANISM: Artificial
<220> FEATURE:
<221> NAME/KEY: PEPTIDE
<222> LOCATION: (1)..(9)
<223> OTHER INFORMATION: Artificial sequence from plant origin

<400> SEQUENCE: 23

Leu Val Tyr Pro Phe Pro Gly Pro Ile
1               5
```

```
<210> SEQ ID NO 24
<211> LENGTH: 9
<212> TYPE: PRT
<213> ORGANISM: Artificial
<220> FEATURE:
<221> NAME/KEY: PEPTIDE
<222> LOCATION: (1)..(9)
<223> OTHER INFORMATION: Artificial sequence from plant origin

<400> SEQUENCE: 24

Tyr Pro Phe Pro Gly Pro Ile Pro Ser
1               5

<210> SEQ ID NO 25
<211> LENGTH: 10
<212> TYPE: PRT
<213> ORGANISM: Artificial
<220> FEATURE:
<221> NAME/KEY: PEPTIDE
<222> LOCATION: (1)..(10)
<223> OTHER INFORMATION: Artificial sequence from plant origin

<400> SEQUENCE: 25

Leu Val Tyr Pro Phe Pro Gly Pro Ile Pro
1               5                   10

<210> SEQ ID NO 26
<211> LENGTH: 10
<212> TYPE: PRT
<213> ORGANISM: Artificial
<220> FEATURE:
<221> NAME/KEY: PEPTIDE
<222> LOCATION: (1)..(10)
<223> OTHER INFORMATION: Artificial sequence from plant origin

<400> SEQUENCE: 26

Val Tyr Pro Phe Pro Gly Pro Ile Pro Asn
1               5                   10

<210> SEQ ID NO 27
<211> LENGTH: 11
<212> TYPE: PRT
<213> ORGANISM: Artificial
<220> FEATURE:
<221> NAME/KEY: PEPTIDE
<222> LOCATION: (1)..(11)
<223> OTHER INFORMATION: Artificial sequence from plant origin

<400> SEQUENCE: 27

Val Tyr Pro Phe Pro Gly Pro Ile Pro Asn Ser
1               5                   10

<210> SEQ ID NO 28
<211> LENGTH: 11
<212> TYPE: PRT
<213> ORGANISM: Artificial
<220> FEATURE:
<221> NAME/KEY: PEPTIDE
<222> LOCATION: (1)..(11)
<223> OTHER INFORMATION: Artificial sequence from plant origin

<400> SEQUENCE: 28

Tyr Pro Phe Pro Gly Pro Ile Pro Asn Ser Leu
1               5                   10

<210> SEQ ID NO 29
<211> LENGTH: 11
<212> TYPE: PRT
```

```
<213> ORGANISM: Artificial
<220> FEATURE:
<221> NAME/KEY: PEPTIDE
<222> LOCATION: (1)..(11)
<223> OTHER INFORMATION: Artificial sequence from plant origin

<400> SEQUENCE: 29

Leu Val Tyr Pro Phe Pro Gly Pro Ile Pro Asn
1               5                   10

<210> SEQ ID NO 30
<211> LENGTH: 12
<212> TYPE: PRT
<213> ORGANISM: Artificial
<220> FEATURE:
<221> NAME/KEY: PEPTIDE
<222> LOCATION: (1)..(12)
<223> OTHER INFORMATION: Artificial sequence from plant origin

<400> SEQUENCE: 30

Val Tyr Pro Phe Pro Gly Pro Ile Pro Asn Ser Leu
1               5                   10

<210> SEQ ID NO 31
<211> LENGTH: 13
<212> TYPE: PRT
<213> ORGANISM: Artificial
<220> FEATURE:
<221> NAME/KEY: PEPTIDE
<222> LOCATION: (1)..(13)
<223> OTHER INFORMATION: Artificial sequence from plant origin

<400> SEQUENCE: 31

Leu Val Tyr Pro Phe Pro Gly Pro Ile Pro Asn Ser Leu
1               5                   10

<210> SEQ ID NO 32
<211> LENGTH: 4
<212> TYPE: PRT
<213> ORGANISM: Artificial
<220> FEATURE:
<221> NAME/KEY: PEPTIDE
<222> LOCATION: (1)..(4)
<223> OTHER INFORMATION: Artificial sequence from plant origin

<400> SEQUENCE: 32

Val Tyr Pro Phe
1

<210> SEQ ID NO 33
<211> LENGTH: 5
<212> TYPE: PRT
<213> ORGANISM: Artificial
<220> FEATURE:
<221> NAME/KEY: PEPTIDE
<222> LOCATION: (1)..(5)
<223> OTHER INFORMATION: Artificial sequence from plant origin

<400> SEQUENCE: 33

Val Tyr Pro Phe Pro
1               5

<210> SEQ ID NO 34
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin
```

```
<400> SEQUENCE: 34

Val Tyr Pro Phe Pro Gly Pro
1               5

<210> SEQ ID NO 35
<211> LENGTH: 33
<212> TYPE: PRT
<213> ORGANISM: Artificial
<220> FEATURE:
<221> NAME/KEY: PEPTIDE
<222> LOCATION: (1)..(33)
<223> OTHER INFORMATION: Artificial sequence from plant origin

<400> SEQUENCE: 35

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Phe Gln Pro
                20                  25                  30

Phe

<210> SEQ ID NO 36
<211> LENGTH: 5
<212> TYPE: PRT
<213> ORGANISM: Artificial
<220> FEATURE:
<221> NAME/KEY: PEPTIDE
<222> LOCATION: (1)..(5)
<223> OTHER INFORMATION: Artificial sequence from plant origin

<400> SEQUENCE: 36

Gln Pro Gln Leu Pro
1               5

<210> SEQ ID NO 37
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 37

Tyr Pro Gln Pro Gln Leu Pro
1               5

<210> SEQ ID NO 38
<211> LENGTH: 4
<212> TYPE: PRT
<213> ORGANISM: Artificial
<220> FEATURE:
<221> NAME/KEY: PEPTIDE
<222> LOCATION: (1)..(4)
<223> OTHER INFORMATION: Artificial sequence from plant origin

<400> SEQUENCE: 38

Gln Pro Gln Pro
1

<210> SEQ ID NO 39
<211> LENGTH: 6
<212> TYPE: PRT
<213> ORGANISM: Artificial
<220> FEATURE:
<221> NAME/KEY: PEPTIDE
<222> LOCATION: (1)..(6)
<223> OTHER INFORMATION: Artificial sequence from plant origin
```

```
<400> SEQUENCE: 39

Pro Gln Pro Gln Leu Pro
1               5

<210> SEQ ID NO 40
<211> LENGTH: 7
<212> TYPE: PRT
<213> ORGANISM: Artificial
<220> FEATURE:
<221> NAME/KEY: PEPTIDE
<222> LOCATION: (1)..(7)
<223> OTHER INFORMATION: Artificial sequence from plant origin

<400> SEQUENCE: 40

Tyr Pro Gln Pro Gln Leu Pro
1               5

<210> SEQ ID NO 41
<211> LENGTH: 8
<212> TYPE: PRT
<213> ORGANISM: Artificial
<220> FEATURE:
<221> NAME/KEY: PEPTIDE
<222> LOCATION: (1)..(8)
<223> OTHER INFORMATION: Artificial sequence from plant origin

<400> SEQUENCE: 41

Pro Tyr Gln Pro Gln Leu Pro Tyr
1               5

<210> SEQ ID NO 42
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 42

Pro Gln Pro Gln Leu Pro Tyr Pro Gln Pro Gln Leu Pro Tyr
1               5                   10

<210> SEQ ID NO 43
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 43

Pro Gln Pro Gln Leu Pro Tyr Pro Gln Pro Gln Leu Pro Tyr
1               5                   10

<210> SEQ ID NO 44
<211> LENGTH: 12
<212> TYPE: PRT
<213> ORGANISM: Artificial
<220> FEATURE:
<221> NAME/KEY: PEPTIDE
<222> LOCATION: (1)..(12)
<223> OTHER INFORMATION: Artificial sequence from plant origin

<400> SEQUENCE: 44

Gln Leu Gln Pro Phe Pro Gln Pro Gln Leu Pro Tyr
1               5                   10
```

```
<210> SEQ ID NO 45
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 45

Pro Phe Arg Pro Gln Gln Pro Tyr Pro Gln Pro Gln Pro Gln
1               5                   10

<210> SEQ ID NO 46
<211> LENGTH: 16
<212> TYPE: PRT
<213> ORGANISM: Artificial
<220> FEATURE:
<221> NAME/KEY: PEPTIDE
<222> LOCATION: (1)..(16)
<223> OTHER INFORMATION: Artificial sequence from plant origin

<400> SEQUENCE: 46

Gln Pro Gln Gln Pro Gln Gln Ser Phe Pro Gln Gln Arg Pro Phe
1               5                   10                  15

<210> SEQ ID NO 47
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 47

Gln Gln Pro Tyr Pro Gln Gln Pro Gln Gln Pro Phe Pro Gln
1               5                   10

<210> SEQ ID NO 48
<211> LENGTH: 15
<212> TYPE: PRT
<213> ORGANISM: Artificial
<220> FEATURE:
<221> NAME/KEY: PEPTIDE
<222> LOCATION: (1)..(15)
<223> OTHER INFORMATION: Artificial sequence from plant origin

<400> SEQUENCE: 48

Val Gln Gly Gln Gly Ile Ile Gln Pro Gln Gln Pro Ala Gln Leu
1               5                   10                  15

<210> SEQ ID NO 49
<211> LENGTH: 15
<212> TYPE: PRT
<213> ORGANISM: Artificial
<220> FEATURE:
<221> NAME/KEY: PEPTIDE
<222> LOCATION: (1)..(15)
<223> OTHER INFORMATION: Artificial sequence from plant origin

<400> SEQUENCE: 49

Gln Gln Pro Pro Phe Ser Gln Gln Gln Gln Pro Leu Pro Gln
1               5                   10                  15

<210> SEQ ID NO 50
<211> LENGTH: 15
<212> TYPE: PRT
```

```
<213> ORGANISM: Artificial
<220> FEATURE:
<221> NAME/KEY: PEPTIDE
<222> LOCATION: (1)..(15)
<223> OTHER INFORMATION: Artificial sequence from plant origin

<400> SEQUENCE: 50

Gln Gln Pro Pro Phe Ser Gln Gln Gln Ser Pro Phe Ser Gln
1               5                   10                  15

<210> SEQ ID NO 51
<211> LENGTH: 21
<212> TYPE: PRT
<213> ORGANISM: Artificial
<220> FEATURE:
<221> NAME/KEY: PEPTIDE
<222> LOCATION: (1)..(21)
<223> OTHER INFORMATION: Artificial sequence from plant origin

<400> SEQUENCE: 51

Gln Gln Val Ser Gln Pro Gln Val Pro Gln Gln Gln Val Pro Gln
1               5                   10                  15

Gln Pro Gln Gln Phe
            20

<210> SEQ ID NO 52
<211> LENGTH: 21
<212> TYPE: PRT
<213> ORGANISM: Artificial
<220> FEATURE:
<221> NAME/KEY: PEPTIDE
<222> LOCATION: (1)..(21)
<223> OTHER INFORMATION: Artificial sequence from plant origin

<400> SEQUENCE: 52

Gln Pro Gln Pro Phe Pro Gln Gln Ser Glu Gln Ser Gln Gln Pro Phe
1               5                   10                  15

Gln Pro Gln Pro Phe
            20

<210> SEQ ID NO 53
<211> LENGTH: 13
<212> TYPE: PRT
<213> ORGANISM: Artificial
<220> FEATURE:
<221> NAME/KEY: PEPTIDE
<222> LOCATION: (1)..(13)
<223> OTHER INFORMATION: Artificial sequence from plant origin

<400> SEQUENCE: 53

Gln Gln Pro Phe Val Gln Gln Gln Pro Phe Val Gln
1               5                   10

<210> SEQ ID NO 54
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 54

Gln Gln Pro Phe Val Glu Gln Gln Glu Gln Pro Phe Val Gln
1               5                   10

<210> SEQ ID NO 55
<211> LENGTH: 14
```

```
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 55

Gln Gln Pro Phe Val Gln Gln Gln Gln Pro Phe Val Gln Gln
1               5                   10

<210> SEQ ID NO 56
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 56

Gln Gln Phe Pro Gln Pro Gln Gln Pro Phe Pro Gln Gln Pro
1               5                   10

<210> SEQ ID NO 57
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 57

Pro Gln Gln Pro Phe Pro Gln Pro Gln Gln Pro Phe Arg Gln
1               5                   10

<210> SEQ ID NO 58
<211> LENGTH: 14
<212> TYPE: PRT
<213> ORGANISM: Artificial
<220> FEATURE:
<221> NAME/KEY: PEPTIDE
<222> LOCATION: (1)..(14)
<223> OTHER INFORMATION: Artificial sequence from plant origin

<400> SEQUENCE: 58

Gln Pro Phe Pro Gln Pro Gln Gln Pro Phe Pro Gln Ser Gln
1               5                   10
```

USE OF PROLINE SPECIFIC ENDOPROTEASES TO HYDROLYSE PEPTIDES AND PROTEINS

This application is the US national phase of international application PCT/EP2004/010782 filed 23 Sep. 2004 which designated the U.S. and claims benefit of EP 03078012.6 and EP 03078496.1, dated 23 Sep. 2003 and 6 Nov. 2003, respectively, the entire content of which is hereby incorporated by reference.

FIELD OF THE INVENTION

The present invention relates to the proteolytic hydrolysis of a peptide or polypeptide.

BACKGROUND OF THE INVENTION

Proline rich dietary proteins such as caseins in bovine milk or glutens in cereals are known to resist proteolytic degradation in the human gastrointestinal tract. As a result proline rich peptides can build up and may lead to undesirable effects in specific groups of individuals. Some of these effects have been ascribed to the fact that the proline rich peptides act as opioids that bind to receptors in peripheral tissues and the central nervous system. For example, syndromes shown by autistic and schizophrenic patients have been linked with the consumption of proline rich dietary proteins. Other effects are the result of an intolerance for proline rich peptides. For example specific proline rich sequences are responsible for the observed toxicity of gluten in celiac disease. Celiac disease is a widely prevalent autoimmune disease of the small intestine which can only be treated by a life-long gluten free diet. Celiac disease is occasionally also accompanied by psychiatric and neurological symptoms illustrating the far-reaching consequences a disturbed metabolism of proline rich peptides may have.

Proteins in bovine milk are associated with growth and health and form an important ingredient in the human diet. Casein constitutes approximately 80% of the total protein in bovine milk and is an important source of amino acids, calcium and phosphate. Casein consists of roughly 50% of alpha-caseins, 35% of beta-caseins, 13% of kappa-caseins and 3% of gamma-caseins. In human milk the alpha-casein fraction is generally absent.

It is known that upon metabolisation of casein a number of new bioactive peptides are formed. From the alpha and beta-casein fractions opioid peptides called alpha-casomorphins and beta-casomorphins, respectively, have been identified and isolated. The pharmacological effects of especially the beta-casomorphins have been extensively studied. The beta-casomorphin with the sequence Tyr-Pro-Phe-Pro-Gly-Pro-Ile (SEQ ID NO:15) is the principal opioid peptide in bovine milk and is called BCM-7 (beta-casomorphin (1-7); Chang et al. (1985) Journal of Biological Chemistry, 260, 9706-9712). Apart from this BCM-7 fragment at amino acid positions 60-66 of the beta-casein molecule, smaller fragments of BCM-7 like Tyr-Pro-Phe-Pro (beta-casomorphin (1-4)) (SEQ ID NO:16) and Tyr-Pro-Phe-Pro-Gly (beta-casomorphin (1-5)) SEQ ID NO:17) at amino acid positions 60-63 and 60-64 respectively as well as all larger BCM-7 related peptides up to a chain length of 11 amino acids (at amino acid positions 60-70) display at least some degree of opioid activity. The N-terminal tripeptide of BCM-7, i.e. the sequence Tyr-Pro-Phe at position 60-62, has no opioid activity. A genetic beta-casein variant called A1 (having a histidine rather than the proline residue of A2 beta-casein at amino acid position 67) is claimed to lead to the formation of increased levels of the BCM-7 molecule.

The basic reason for the generation of the various beta-casomorphins is that their amino acid sequence is relatively rich in proline residues. Because peptide bonds involving proline residues resist proteolytic breakdown, the beta-casomorphin sequences tend to survive exposure to the gastrointestinal proteases in the stomach and the intestinal lumen. For the same reason one may assume that these beta-casomorphin sequences tend to survive incubations with other proteases, for example those proteases commonly used in the industrial production of protein hydrolysates. This assumption implies that the commonly available protein hydrolysates or products containing these protein hydrolysates all contain the BCM-7 or closely related peptides. As the BCM-7 peptide fragment and its related molecules have been linked with certain diseases, the presence of such molecules in protein hydrolysates, quite often used in the diet of vulnerable groups like infants, elderly and patients, is an undesirable situation. Results of opiate receptor binding assays of human and bovine beta-casomorphins indicate that the fragments with opioid activity bind with opiate receptors in the rat brain membrane. It has been shown that the beta-caseins are more selective towards mu-ligands with little affinity for delta- and kappa-receptor subtypes. According to these and other studies beta-casomorphins are claimed to have various gastrointestinal, analgesic, respiratory, cardiovascular, endocrine and immunomodulatory effects. A common structural feature of opioid peptides incorporating a proline residue is the Tyr-Pro-Phe/Trp motif (Okada et al, Vitamins and Hormones 2002, 65, 257-279).

Although in normal individuals the peptidases in the intestinal epithelial layer and in the blood can cope with the beta-casomorphins, this seems not to be always the case for patients suffering from schizophrenia, autism, ADHD or other mood disorders. For example, genetic alterations in plasma dipeptidyl peptidase IV (DPP IV) enzyme activity leading to an incomplete breakdown of proline rich peptides have been linked with the occurrence of these diseases. Moreover hyperpeptiduria, i.e. an increased concentration of casein or gluten derived peptides in the urine, is regularly found (Reichelt, W. H. et al; (1997) Dev. Brain Dysfunct; 10: 44-55). Recent scientific literature provides compelling evidence that an incomplete degradation of proline rich peptides may contribute to the development and the severity of such diseases. Apart from the caseine derived BCM-7 fragment, also gluten derived protease resistant peptides have been mentioned in this connection. Already in 1979 Panksepp (Trends in Neuroscience 1979; 2:174-177) proposed the opioid excess theory in which he suggested that a disturbed opioid metabolism is part of the pathogenesis in autism. Nowadays we understand that many proline rich peptides are highly resistant to cleavage by gastric and pancreatic peptidases such as pepsin, trypsin, chymotrypsin and the like and that only specific enzymes, as present in amongst others the brush border epithelial layer of the gastrointestinal tract, are capable of hydrolysing peptide bonds involving proline.

Gluten is the insoluble protein fraction of cereals like wheat, rye, oats, barley, maize and rice that remains after washing to remove starch and water-soluble components. Gluten can be subdivided into 4 major solubility fractions i.e. albumin, globulin, prolamin and glutelin. Among these especially the prolamin and the glutelin fractions of wheat, corn, barley and oats are characterized by relatively high contents of the amino acids proline and glutamine. Recent evidence has implicated the proline rich gluten sequences as a major factor in the development of celiac disease. Celiac disease, also known as celiac sprue, is an autoimmunedisease of the small intestine caused by the ingestion of gluten proteins. It commonly appears in early childhood with severe symptoms like chronic diarrhea and abdominal distension; later in life symptoms include fatigue, weight loss due to malabsorption and neurological symptoms. Among the proline rich fractions of the various cereals, alpha-gliadin from wheat, hordein from barley, secalin from rye and avenin from oats seem to be most toxic (Schuppan, D.; Gastroenterology 2000; 119:234-242). A life-long gluten free diet is the only effective treatment for celiac disease patients. Among celiac patients a high prevalence of various autoimmune disorders, especially type 1 diabetes, dermatitis herpetiformis, autoimmune thyroiditis, collagen diseases, autoimmune alopecia and autoimmune hepatitis has been observed. This indicates that by unknown mechanisms untreated celiac disease predisposes to autoimmunity to other organs (Schuppan, D. 2000 Gasteroenterology 119:234-242). Furthermore there are indications that a mild form of celiac disease is present in a group of people suffering from irritable bowel syndrome (IBS). IBS is a disorder that interferes with the normal functions of the large intestine and is characterized by crampy abdominal pain, constipation and diarrhea. IBS usually begins around the age of 20 and causes a great deal of discomfort and distress. The eating of wheat, barley, rye or milk products has been associated with a worsening of IBS symptoms.

Recently Shan et al (Science; vol 297, 27 September 2002: 2275-2279) identified a gliadin-derived, proline rich, 33 amino acids long peptide thought to be the source of a set of major celiac patient-specific T cell epitopes. Whereas an enzyme extract prepared from small intestine brush-border cells was unable to hydrolyse this 33-mer, suppletion with a bacterial prolyl oligopeptidase from Flavobacterium meningosepticum led to a rapid digestion with a concomitant strongly decreased stimulation of a relevant Tcell clone. In imitation of earlier work on the oral administration of papain (Messer, M. and Baume, P. E.; Lancet 1976; 2:1022), the article indicates the potential of the prolyl oligopeptidase as a dietary enzyme in detoxifying gluten by enzyme therapy.

Prolyl oligopeptidases (EC 3.4.21.26) have the unique possibility of preferentially cleaving peptides at the carboxyl side of proline residues. In the prolyl oligopeptidases isolated from mammalian sources as well as in the prolyl oligopeptidase isolated from Flavobacterium meningosepticum a unique peptidase domain has been identified that excludes large structured proteins from the enzyme's active site. In fact these enzymes are unable to degrade proteins containing more than about 30 amino acid residues so that these enzymes are now referred to as "prolyl oligopeptidases" (Fulop et al: Cell, Vol. 94, 161-170, Jul. 24, 1998). All known prolyl oligopeptidases are cytosolic enzymes that exhibit pH optima near neutrality and are characterized by the fact that they cannot efficiently degrade molecules containing more than approximately 30 amino acid residues. The fact that these enzymes exhibit pH optima that correspond with the pH values prevailing in the more distal part of the gastrointestinal tract, makes them ideally suitable as dietary supplements supporting the intestinal digestion process of dietary gluten.

Another enzyme that can have a benefit in the inactivation of toxic proline rich peptides, is the enzyme dipeptidyl peptidase IV (US2002/0041871A). Dipeptidylpeptidase IV, also called Xaa-Pro-dipeptidyl-aminopeptidase (EC 3.4.14.5) catalyzes the release of an N-terminal dipeptide, Xaa-Xbb from a peptide with the N-terminal sequence Xaa-Xbb-Xcc-, preferentially when Xbb is proline and provided Xcc is not proline. Dipeptidyl-peptidase IV has been isolated from a large number of mammalian sources, for example the intestinal brush border membranes form a rich source of the enzyme. Furthermore the enzyme has been isolated from microbial sources such as the food grade microorganisms Saccharomyces, Lactococcus and Aspergillus. Like the prolyl oligopeptidases, all known dipeptidyl-peptidases IV are enzymes with near neutral pH optima and thus suited for supporting the intestinal digestion process.

Because of the possible implications of the proline specific oligopeptidase and the dipeptidyl-peptidase IV in the treatment of celiac disease or schizophrenia, autism or other mood disorders, these data have resulted in a number of patent applications that deal with various aspects of this matter. For example U.S. Pat. No. 6,447,772 and WO 01/24816 describe compositions containing dipeptidyl peptidase IV, WO 03/068170 describes compositions containing proline specific oligopeptidases optionally combined with dipeptidyl-peptidase IV, WO 02/45523 describes low allergenic protein hydrolysates prepared with proline specific endoproteases and WO 03/028745 describes compositions comprising bacterial strains that can lower the concentration of intestinal toxic proline rich peptides. WO 96/36239 describes the advantages of products derived from cattle substantially free of the beta-casein A1 allele.

SUMMARY OF THE INVENTION

The present invention relates to a process for the proteolytic hydrolysis of a peptide or a polypeptide, said peptide or polypeptide comprising 4 to 40, preferably 5 to 35, amino acid residues and said peptide or polypeptide is not hydrolysable by subtilisin whereby said peptide or polypeptide is hydrolysed by a proline specific endo protease at a pH of 6.5 or lower, preferably 5.5 or lower and more preferably 5.0 or lower to hydrolyse said peptide or polypeptide. Preferably at least 70%, more preferably at least 80%, and most preferably at least 90% of the peptide or polypeptide is hydrolysed in this process.

According to another embodiment the process of the invention relates to a process for the proteolytic hydrolysis of a peptide or a polypeptide, said peptide or polypeptide comprising 4 to 40, preferably 5 to 35, amino acid residues and comprises the tripeptide motif Glu-Xxx-Pro, Gln-Xxx-Pro, Tyr-Pro-Phe or Tyr-Pro-Trp whereby said peptide or polypeptide is hydrolysed by a proline specific endo protease at a pH of 6.5 or lower, preferably 5.5 or lower and more preferably 5.0 or lower to hydrolyse said peptide or polypeptide. Preferably at least 70%, more preferably at least 80%, and most preferably at least 90% of the peptide or polypeptide is hydrolysed in this process.

Moreover the present invention provides a process for the proteolytic hydrolysis of a peptide or a polypeptide, said peptide or polypeptide comprising 4 to 40, preferably 5 to 35 amino acid residues, and whereby the amino acid residues of the peptide or polypeptide comprises for at least 30%, preferably at least 40%, proline and/or glutamine residues whereby said peptide or polypeptide is hydrolysed by a proline specific endo protease at a pH of 6.5 or lower, preferably 5.5 or lower and more preferably 5.0 or lower to hydrolyse said peptide or polypeptide with the proviso that the peptide or polypeptide comprises at least 10% of proline residues. Preferably at least 70%, more preferably at least 80%, and most preferably at least 90% of the peptide or polypeptide is hydrolysed in this process.

Preferably the peptide or polypeptide in the process of the invention comprises the motif Gln-Xxx-Pro or Glu-Xxx-Pro and contains 9 or more amino acid residues. This peptide or polypeptide is advantageously hydrolysed into a peptide containing 8 or less amino acid residues. In case the peptide or polypeptide has the motif Tyr-Pro-Phe or Tyr-Pro-Trp, preferably the bond between Pro and Phe or Pro and Trp is hydrolysed.

The preferred endoproline specific endo protease used in the process of the invention is preferably a proline specific endo protease derived from *Aspergillus* or belonging to the S28 family of serine proteases. This enzyme has preferably a pH optimum below 6.5, preferably below 5.5, more preferably below 5.0 to hydrolyse a peptide or polypeptide comprising 4 to 40, preferably 5 to 35, amino acid residues that is not hydrolysable by subtilisin.

The proline specific endoprotease can be used to hydrolyse at pH of below 5.5, proline rich peptides which are brought in relation with psychiatric disorders including autism, schizophrenia, ADHD, bipolar mood disorder and depression and celiac disease linked disorders like autoimmune disorders, especially type 1 diabetes, dermatitis herpetiformis, autoimmune thyroiditis, coliagen diseases, autoimmune alopecia and autoimmune hepatitis and IBS.

Advantageously this enzyme is used to produce food, for example beer or bread which is devoid of celiac related epitopes, preferably gluten epitopes, more preferably wheat or barley epitopes.

The present invention also relates to proline specific endoprotease for use as a medicament or for the use in manufacturing a medicament, which preferably is an *Aspergillus*, more preferably an *Aspergillus niger* enzyme.

According to another embodiment of the invention a proline specific endoprotease is used for the manufacture of a dietary supplement or a medicament for treatment or prevention of psychiatric disorders including autism, schizophrenia, ADHD, bipolar mood disorder and depression and celiac disease linked disorders like autoimmune disorders, especially type 1 diabetes, dermatitis herpetiformis, autoimmune thyroiditis, collagen diseases, autoimmune alopecia and autoimmune hepatitis and IBS Advantageously a proline specific endoprotease is used for the manufacture of a dietary supplement or a medicament for individuals below the age of 25 years.

According to the present invention a proline specific endoprotease is also used for a dietary supplement or a medicament for treatment or preventing of psychiatric disorders including autism, schizophrenia, ADHD, bipolar mood disorder and depression and celiac disease linked disorders like autoimmune disorders, especially type 1 diabetes, dermatitis herpetiformis, autoimmune thyroiditis, collagen diseases, autoimmune alopecia and autoimmune hepatitis and IBS.

Furthermore the present invention relates to the use of proline specific endoprotease to hydrolyse protein or peptides having more than 30 amino acid residues. In the uses according to the invention, preferably *Aspergillus*, more preferably *A. niger* proline specific endoprotease is applied.

The present invention also relates to the use of a proline-specific protease that is active at a pH of 5 or below 5 in the presence of pepsin.

Advantageously the present invention relates to a process for the proteolytic hydrolysis of said peptides or protein present in milk proteins obtained from cattle carrying the beta-casein A1 or the beta-casein A2 allele.

Protein can also be used in the process of the invention. First the protein has to be hydrolysed into peptides comprising 4 to 40 amino acid residues. The hydrolysis of protein can be done prior to or simultaneous with the process of the present invention.

Furthermore the present invention relates to the use of a proline specific endoprotease having a pH optimum below 6.5, preferably below 5.5, more preferably below 5.0 as a dietary supplement, as a medicament, for the production of a dietary supplement, for the production of medicament or for the production of feed including pet food, intended for a non-human animal, preferably a mammal.

DETAILED DESCRIPTION OF THE INVENTION

In general the prior art aims at either the removal of toxic proline rich peptides from food prior to consumption or at the oral supply of corrective enzymes to compensate for an inadequate intestinal digestion process. In a normal gastrointestinal digestion process, proteolysis in the stomach by the enzyme pepsin is understood to be the first step in the breakdown of dietary proteins. The second step takes place in the small intestine, i.e. the duodenum and the jejunum located immediately downstream of the stomach. In the duodenum the acid pH of the stomach contents is raised by the addition of pancreatic juices also containing a variety of endo- and carboxypeptidases. Catalysed by the latter enzymes a further breakdown of pepsin degraded dietary protein is accomplished in the lumen of duodenum and jejunum at pH values above 5. Prior to transport over the intestinal wall, a third step involves a further peptide hydrolysis in the brush border surface membrane of the intestestinal epithelium. The latter step is accomplished by a number of proteases including DPP IV that are localized in the membranes of these epithelial cells. The prior art suggests that in the intestine of individuals suffering from some of the diseases the present invention is aiming at, some of these epithelial enzymes and notably DPP IV is partly inactive or not even present. In celiac patients the levels of these epithelial enzymes are probably normal but within this group of individuals even low levels of certain proline rich peptides can elicit an strong inflammatory T-cell response. The solution presented in prior art is that orally corrective enzymes are introduced into the human gut in order to minimise the levels of toxic proline rich peptides present in the lumen of the gut. In this approach the prior art has selected enzymes that imitate the natural human enzymes as much as possible i.e. the enzymes are active in the gut under conditions above pH 5. These prior art enzymes are not active under acidic conditions or the oral presentation forms containing these prior art enzymes are adequately coated to prevent their activity under acid conditions.

The present inventors have found that an enzyme deploying its main activity under acid conditions in the stomach offers a superior solution for the problem of insufficiently digested proline rich peptides. This approach is new and opens the possibility of using other enzymes than the ones mentioned in the literature for solving the problem.

As discussed above several publications point towards the possibilities of using enzymes like dipeptidyl peptidase IV and prolyl oligopeptidase in preventing a disturbed opioid metabolism. Thereto dipeptidyl peptidase IV as well as the prolyl oligopeptidase enzymes are selected that typically are active under near neutral pH conditions. The implication is that these enzymes will only efficiently hydrolyse proline rich proteins under conditions above pH 5. Taking the pH profile of the human gastrointestinal tract into consideration, these prior art enzymes will not become active before reaching the distal part of the duodenum, i.e. well beyond the stomach. However, the distal part of the duodenum is a major site for protein absorption and is also known to be affected in celiac disease patients. So in fact these prior art enzymes will start to work where part of the damage is done.

Furthermore the prior art enzymes become active only after a significant pre-degradation of proline rich proteins. The time required to achieve this pre-degradation by pancreatic enzymes further limits the period available for the orally applied enzymes to achieve a complete hydrolysis of proline rich sequences. According to the present invention an enzyme is used that can degrade most of the proline rich and/or glutamine rich protein sequences before the food enters the small intestine. The normal food residence time in the stomach provides the time period required for an adequate hydrolysis of proline rich or glutamine rich proteins. Furthermore according to the present invention preferably an enzyme is used that is able to cleave peptides at the carboxyl side of proline residues and is also able to cleave intact proteins at the carboxyl side of proline residues and even in the presence of pepsin. Prior art enzymes will be hydrolysed under the low pH conditions of the stomach and if exposed to the proteolytic pepsin enzyme that is secreted into the stomach. However up to now the use of such an acid/pepsin stable enzyme is not known in the present process. The present approach will result in the substantial breakdown of proline rich peptides, polypeptides and proteins before the intestine is reached instead of the prior art approach which suggests to mimic the natural process of hydrolysing proline rich peptides in the intestine. The preferred enzyme used in the process of the invention is an enzyme that is active at pH values below 5 in the presence of pepsin and is capable to break down dietary proteins or polypeptides as well as peptides. The prior art solutions always need a co-enzyme that prehydrolyses the dietary protein into peptides and only thereafter the additional proline specific enzymes can start to deploy their activity.

A "peptide" or "oligopeptide" is defined herein as a chain of two to thirty amino acid residues that are linked through peptide bonds. The terms "peptide" and "oligopeptide" are considered synonymous (as is commonly recognized) and each term can be used interchangeably as the context requires. A "polypeptide" is defined herein as a chain containing more than 30 amino acid residues.

Peptides or polypeptides having four to forty amino acid residues that are not hydrolysable by subtilisin (EC3.4.21.62), preferably subtilisin Carlsberg are understood to be peptides or polypeptides that after an incubation of 2 hours at pH 8.0 and 60 degrees C. in a suspension or solution containing 20 g/l protein and an enzyme to substrate ratio of 0.12 AU-A (Anson Units Alcalase) Protease Units per gram protein remain intact. The AU-A Protease Unit is defined as specified in the Analytical Method LUNA #2003-32153-01 as issued by Novozymes (Denmark). Intact meaning that after the incubation the original peptide or polypeptide forms more than 80%, preferably more than 90%, more preferably more than 95% of the resulting enzyme reaction products. In practice the enzyme digestion is carried out under the conditions indicated and using 40 microliter of Alcalase per gram of substrate protein present. Examples of such a non-hydrolysable peptide is the VYPFPGPIPN (SEQ ID NO:1) peptide resulting from the beta-casein hydrolysis described in Example 4. Another example of such a non-hydrolysable polypeptide is the 33-mer described in Example 6.

An oligopeptidase is an enzyme classified as EC 3.4.21.26 and belonging to the family of serine proteases clan SC, family S9.

All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989). The amino acid Xxx, Xaa, Xbb or Xcc is meant to be any amino acid. By a motif is meant an amino acid sequence, which is part of a peptide, polypeptide or protein. Herein glutamine (Q or Gln) is understood be glutamine or glutamate (E or Glu). For example, in chemical deamidated gluten a large part of natural glutamine residues present is converted into glutamate. So the motif Gln-Xxx-Pro is also comprising the motif Glu-Xxx-Pro. Also in other peptide, polypeptide or protein glumine can be converted into glutamate, for example due to pH conditions, temperature or by enzymatic conversion for example by trans glutaminase.

By a proline rich peptide or polypeptide is meant a peptide or polypeptide comprising 4 to 40 amino acid residues whereby the amino acid residues of the peptide or polypeptide comprises for at least 30%, preferably at least 40% of proline and/or glutamine residues with the proviso that the peptide or polypeptide comprises at least 10% of proline residues. A dietary supplement is according to the adapted definition of the DSHEA, a product (other than tobacco) that is intended to supplement the diet that bears or contains one or more of the following dietary ingredients: a protein including an enzyme, a polypeptide, a peptide, a vitamin, a mineral, an herb or other botanical, an amino acid, a dietary substance for use by man to supplement the diet by increasing the total intake, or a concentrate, metabolite, constituent, extract, or combinations of these ingredients.

Moreover a dietary supplement is intended for ingestion in pill, capsule, tablet, or liquid form.

is not represented for use as a conventional food or as the sole item of a meal or diet.

is, in general, labelled as a "dietary supplement".

includes products such as an approved new drug, certified antibiotic, or licensed biologic that was marketed as a dietary supplement of food before approval, certification, or license (unless the Secretary of Health and Human Services waives this provision).

Toxic proline rich peptides or polypeptides are peptides or polypeptides implicated in the binding to opioid receptors or in the development or the severity of psychiatric or celiac disorders.

Psychiatric disorders include autism, schizophrenia, ADHD, bipolar mood disorder as well as depression.

Celiac disease linked disorders are autoimmune disorders, especially type 1 diabetes, dermatitis herpetiformis, autoimmune thyroiditis, collagen diseases, autoimmune alopecia and autoimmune hepatitis.

The internationally recognized schemes for the classification and nomenclature of all enzymes from IUMB include proteases. The updated IUMB text for protease EC numbers are found on the internet. In this system enzymes are defined by the fact that they catalyse a single reaction. The system categorises the proteases into endo- and exoproteases. Endoproteases are those enzymes that hydrolyse internal peptide bonds, exoproteases hydrolyse peptide bonds adjacent to a terminal α-amino group ("aminopeptidases"), or a peptide bond between the terminal carboxyl group and the penultimate amino acid ("carboxypeptidases"). The endoproteases are divided into sub-subclasses on the basis of catalytic mechanism. There are sub-subclasses of serine endoproteases (EC 3.4.21), cysteine endoproteases (EC 3.4.22), aspartic endoproteases (EC 3.4.23), metalloendoproteases (EC 3.4.24) and threonine endoproteases (EC 3.4.25).

WO 02/45524 describes a proline specific endoprotease obtainable from *Aspergillus niger*. Surprisingly we have found now that this *Aspergillus* enzyme is advantageously used in the present process under the acid conditions in the stomach and can hydrolyse intact dietary proteins, polypeptides as well as smaller peptide molecules under these conditions as well. Furthermore this enzyme survives the presence of the enzyme pepsin under acid conditions and is likely to continue its activity throughout the duodenum. We demonstrate that the *A. niger* derived proline specific endoprotease is quite different from the known proline specific proteases as well as the glutenases specified in WO 03/068170, from an activity as well as from an evolutionary point of view. The latter feature is amply demonstrated by the fact that the amino acid sequence homologies between the glutenases specified in WO 03/068170 and the *A. niger* derived enzyme are typically below 20% using a global alignment algorithm analysis. This result is in accordance with the current view that prolyl oligopeptidases do not occur in fungi such as *Aspergillus niger* from which the proline specific endoprotease according to the present invention is isolated (Venäläinen, J. I. et al, Eur J Biochem 271, 2705-2715 (2004)).

By the proline specific endo protease according to the invention or used according to the invention is meant for example the polypeptide as mentioned in claims 1-5, 11 and 13 of WO 02/45524 which is incorporated here by reference. Therefore this proline specific endo protease is a polypeptide which has proline specific endoproteolytic activity, selected from the group consisting of:

(a) a polypeptide which has an amino acid sequence which has at least 40% amino acid sequence identity with amino acids 1 to 526 of SEQ ID NO:2 or a fragment thereof;

(b) a polypeptide which is encoded by a polynucleotide which hybridizes under low stringency conditions with (i) the nucleic acid sequence of SEQ ID NO:1 or a fragment thereof which is at least 80% or 90% identical over 60, preferably over 100 nucleotides, more preferably at least 90% identical over 200 nucleotides, or (ii) a nucleic acid sequence complementary to the nucleic acid sequence of SEQ ID NO:1. The SEQ ID NO:1 and SEQ ID NO:2 as shown in WO 02/45524. Preferably the polypeptide is in isolated form.

The preferred polypeptide has an amino acid sequence which has at least 50%, preferably at least 60%, preferably at least 65%, preferably at least 70%, more preferably at least 80%, even more preferably at least 90%, most preferably at least 95%, and even most preferably at least about 97% identity with amino acids 1 to 526 of SEQ ID NO: 2 or comprising the amino acid sequence of SEQ ID NO:2.

Preferably the polypeptide is encoded by a polynucleotide that hybridizes under low stringency conditions, more preferably medium stringency conditions, and most preferably high stringency conditions, with (i) the nucleic acid sequence of SEQ ID NO:1 or a fragment thereof, or (ii) a nucleic acid sequence complementary to the nucleic acid sequence of SEQ ID NO: 1.

The term "capable of hybridizing" means that the target polynucleotide of the invention can hybridize to the nucleic acid used as a probe (for example, the nucleotide sequence set forth in SEQ. ID NO: 1, or a fragment thereof, or the complement of SEQ ID NO: 1) at a level significantly above background. The invention also includes the polynucleotides that encode the proline specific endoprotease of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO:1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 20 fold, more preferably at least 50 fold, and even more preferably at least 100 fold, as intense as interactions between other polynucleotides and the coding sequence of SEQ ID NO: 1. The intensity of interaction may be measured, for example, by radiolabelling the probe, for example with $^{32}P$. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available on the internet through the National Center for Biotechnology Information This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold. These initial neighbourhood word hits act as seeds for initiating searches to find HSPs containing them. The word hits are extended in both directions along each sequence for as far as the, cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The enzyme according to the invention is preferably obtained from a fungus, preferably an *Aspergillus*, more preferably from *Aspergillus niger*. So, the *Aspergillus* derived enzyme is found to be a true endoprotease that is acid stable and preferably not affected by the presence of pepsin under pH conditions that prevail in the stomach. Proline specific oligopeptidases in general including the enzyme as can be obtained from *Flavobacterium meningosepticum* have almost no activity at and below pH 5 and are inactivated by the combination of a low pH and the presence of the enzyme pepsin. Furthermore proline specific proteases in general are unable to degrade intact proteins and were found to efficiently hydrolyse smaller peptides only, i.e. peptides up to a length of approximately 30 amino acid residues.

The present invention provides economical, food grade compositions to defer or to minimise the phenomena of toxic proline rich peptides or of a disturbed opioid metabolism. The compositions include oral enzyme formulations suited for alimentary, pharmaceutical and veterinary use as well as enzyme formulations suited for the production of protein hydrolysates and food products with significantly lowered levels of opioid or toxic proline rich peptides.

The present invention discloses methods to hydrolyse proline rich peptides or polypeptides which are brought in relation with the development of psychiatric disorders or celiac disease or of a disturbed opioid metabolism. The present invention also discloses methods to produce foods that can prevent or delay the development of such disorders in infants or in general for individuals below the age of 25 years. Also foods that are better tolerated by people suffering from celiac disease and abdominal symptoms associated with IBS can be prepared by such methods. An embodiment of the present invention is related to the breakdown of these proline rich peptides or polypeptides before consumption hereby preventing or minimising exposure of the body to toxic proline rich peptides. In infants this will avoid an early exposure to opioids and the immature immune system will not be sensitised by such toxic proline rich peptides. Also for teenagers and adults a diet containing reduced levels of toxic proline rich peptides will have prophylactic benefits, e.g. for people suffering from an unnoticed celiac disease or from IBS. The invention also relates to the suppletion of a suitable enzyme for the breakdown in the body (human or animal) of these toxic proline rich peptides or peptides in the stomach, i.e. under acid pH conditions, preferably under conditions below pH 5. According to the latter embodiment persons suffering from celiac disease, diseases associated with the occurrence of celiac disease or diseases caused by a decreased level of body proline specific proteases required for the breakdown of these peptides or polypeptides, are capable to degrade the relevant proline rich peptides or polypeptides in the stomach and in the proximal part of the duodenum. Moreover the enzymes according to the present invention do not require protective coatings.

Preferably at least 80% of the toxic proline rich peptides or polypeptides which are formed upon an incubation of peptides or polypeptides or protein with subtilisin (EC 3.4.21.62) preferably a *Bacillus licheniformis* subtilisin (or subtilisin Carlsberg) under neutral pH conditions are hydrolysed by the proline specific endoprotease according to the invention. The formation of such subtilisin resistant peptides is illustrated in Example 4 of this application. Such subtilisin resistant proline rich peptides are often related with the diseases mentioned above. Examples of these peptides are BCM-7, BCM-7 related peptides i.e. peptides comprising the amino acid sequence YPFP (SEQ ID NO:2) as present at position 60 to 63 of the beta-casein molecule. Furthermore gliadin derived peptides comprising the motif Gln-Xxx-Pro (Q-X-P), for example the PYPQPQLPY epitope (SEQ ID NO:5) as well as other subtilisin resistant molecules comprising this Q-X-P or E-X-P motif that can be obtained from gliadin, hordein, secalin or avenin are examples hereof. More preferably at least 90%, still more preferably at least 95% and most preferably at least 99% of proline rich peptides which would be formed by hydrolysis by subtilisin are broken down or are not formed by using the proline specific endoprotease according to the invention. Most preferably these proline rich peptides can be degraded according to the process of the invention under conditions below pH 5.5.

One way of supplying the required enzymes would be in the form of a digestive aid, e.g. as stabilized enzyme formulations that are coingested with the food to help the gastrointestinal digestion of dietary proline rich peptides or polypeptides. Another way would be to prevent or to limit the ingestion of the problematic toxic proline rich sequences, e.g. by using protein food "pre-digested" with *Aspergillus* enzyme. Such protein food could be supplied in the form of a hydrolysate, e.g. a gluten or a milk protein hydrolysate and includes hydrolysates that have been extensively digested by endo- as well as exoproteases to release large quantities of free amino acids A typical example of the latter application would be the generation of gluten hydrolysates rich in glutamate for a.o. savoury applications. The hydrolysate could be consumed as such or could serve as a food ingredient. In another way the invention provides the use of a composition for improving the tolerability of food products characterized in that the composition comprises an acid stable proline-specific endoprotease according to the invention. In yet another way the invention provides a process for preparing a food comprising the addition of an acid stable proline-specific endoprotease for an improved tolerability of a food product. In all such applications the proline specific enzyme would be used as a so-called processing aid.

The strains of the genus *Aspergillus* have a food grade status and enzymes derived from these micro-organisms are known to be from an unsuspect food grade source. According to another preferred embodiment, the enzyme is secreted by its producing cell rather than representing a non-secreted, so called cytosolic or periplasmatic enzyme. In this way enzymes can be recovered from the cell broth in an essentially pure state without expensive purification steps. Preferably the enzyme has a high affinity towards its substrate under the prevailing pH and temperature conditions. Preferably the enzyme is not inactivated by the gastrointestinal proteolytic enzymes such as pepsin or trypsin, elastase and chymotrypsin under the pH conditions of that relevant part of the gastrointestinal tract. More preferably the enzyme is active in the stomach as well as in the duodenum and does not require a protective coating.

The alimentary canal of humans is a sequence of different compartments. Food is ingested and after swallowing, it reaches the stomach where it is mixed with acid and the endoprotease pepsin. Typical residence times of solid food in the stomach range from one to a few hours. Occasional opening of the pyloris allows the acidified and partly hydrolysed food to flow into the small intestine. In the first part of the small intestine i.e. in the duodenum, bile as well as pancreatic juice are added. The pancreatic juice contains bicarbonate to partly neutralize the stomach contents. The pancreatic juice also contains an additional set of proteases, i.e. the endoproteases trypsin, chymotrypsin and elastase as well as the carboxypeptidases A and B to further degrade the peptides and polypeptides formed by the pepsin in the stomach. After the duodenum, the digest reaches the jejunum. The duodenum and the jejunum are the major sites for protein absorption in the gastrointestinal tract. This absorption process involves a further proteolytic breakdown of the dietary proteins by different proteases anchored in the brush border cells of the intestinal epithelium. The latter hydrolysis is accompanied by a facilitated transport of small peptides as well as free amino acids over the intestinal wall. The last part of the small intestine is formed by the ileum, after which the digest enters the large intestine (colon). In the colon, there is an intensive fermentation but there is no appreciable absorption of amino acids or peptides.

Ingestion of gluten by celiac disease patients leads to lesions of the proximal small intestine. Atrophy of the intestinal villi is one most characteristic features of such lesions. This villous atrophy is not restricted to the jejunum but can also be demonstrated in the distal duodenum (Meijer, J. W. R. et al; Virchows Arch. 2003 February; 442:124-128). This observation indicates that in celiac patients the damaging effects of toxic proline rich peptides is already apparent in an area immediately downstream of the stomach. We have found that enzyme therapies aiming at the prevention of the symptoms of celiac disease should be aimed at hydrolyzing the relevant proline rich peptides in the stomach rather than in the more distal part of the gastrointestinal tract. Advantageously the activity of the enzyme applied in the enzyme therapy is such that it starts to work in the stomach and continues to be active in the duodenum. We have found that also opioid peptides playing a role in the development of psychiatric, respiratory and cardiovascular disorders are best destroyed in the stomach. As the duodenum and the jejunum are the major sites for protein absorption, the level of toxic peptides in this part of the small intestine should be as low as possible to minimise the symptoms associated with the presence of these toxic peptides.

In the use as digestive aid, the corrective enzyme should be sufficiently active at a temperature of 37 degrees C. and should preferably have a low pH optimum to survive the acid conditions in the stomach. According to published data the acidity of ingested food decreases from an initial pH 5 value to pH 3.5 thirty minutes after ingestion followed by a further decrease to pH 2 sixty minutes after ingestion (thesis Mans Minkus; University of Utrecht, The Netherlands; ISBN:90-393-1666-X). So ideally enzymes intended for enzyme therapy should be active under pH values as low as 2. Studies on gastric emptying indicate that 45 minutes after intake almost 90% of the solid food is still present in the stomach (R. Notivol et al., 1984. Scand J. Gastroenterol. 19: 1107-1113). Beyond the stomach, the pH of the food slowly rises to reach a pH of 5 in the distal part of the duodenum, i.e. approx 50 cm beyond the pyloris (Handbook of Physiology, American Physiological Society, Washington, D.C., 1968, Ed. Werner Heidel; Section 6: Alimentary Canal, Volume 111, pp 1457-1490). In WO 03/068170 different "glutenases" are specified that can decrease the levels of toxic gluten oligopeptides in foodstuffs, either prior to or after ingestion by a patient. The term "glutenase" refers to protease or peptidase enzymes, more specifically prolyl-specific proteases, that are capable of cleaving toxic oligopeptides of gluten proteins into non-toxic fragments. As all of these glutanases mentioned typically are intended to be active in the intestine, they are optimally active under near neutral pH conditions. WO 03/068170 teaches the degradation of toxic proline rich peptides in or beyond the duodenum rather than in the stomach or the proximal part of the duodenum. Moreover WO 03/068170 aims at enzyme preparations protected by so called enteric coatings which mask the enzyme activity at low pH so that the enzymes present will pass through the stomach and only become active in the intestine under neutral pH conditions.

If used as industrial processing aid in the production of protein hydrolysates, the enzyme should be sufficiently active under conditions that allow microbially safe incubations under non-sterile industrial conditions. Adequate enzyme activity at a processing temperature of at least 50 degrees C. and a pH value well below pH 5.5 meets these requirements.

The basidiomycete *Agaricus bisporus* (Sattar et al; J. Biochem. 107, 256-261 (1990)) and the non-related ascomycete *Aspergillus niger* (WO 02/45524) have both been shown to produce an extracellular prolyl endopeptidase. However, the enzyme obtained from the basidiomycete will not survive pH values below 5 and is therefore less attractive. Preferably a prolyl endopeptidase from *A. niger* is used which has an acid pH optimum.

The present invention provides enzyme preparations which combine low costs, legislative acceptance with a proven efficacy under acid pH conditions towards proline rich peptide sequences. Preferably the same enzyme can be used to degrade not only the A1 as well as the A2-type beta-casomorphins but also various gluten epitopes.

This *Aspergillus* derived proline specific endoprotease is found to be very active in breaking down proline rich peptides or polypeptides or even proteins. Advantageously this enzyme is secreted by the producing microorganism into the fermentation broth, has an acid pH optimum and can be produced food grade and in an economic way. The relevant beta-casomorphin peptides contain up to four proline residues in the molecule and, moreover, the A1 and the A2 beta-casomorphins have different amino acid sequences. Quite surprisingly we have found that the *Aspergillus* enzyme is capable of hydrolysing beta-casomorphins at the C-terminal side of the proline at position 61 and thus effectively inactivates all BCM-7 and BCM-7 related peptides, both for A1 or A2 beta-casein. This is quite remarkable because we have found that a widely used and highly aggressive endoprotease with a broad substrate specificity such as subtilisin (EC 3.4.21.64) commercially available as for example Alcalase, is not able to degrade BCM-7. Similarly other industrially available proteases will not be able to degrade BCM-7. In fact the *Aspergillus* derived proline specific endoprotease can hydrolyse beta-casomophine but, quite surprisingly, at only one of the four proline residues present in BCM-7. Nevertheless, because of the specificity of this particular *Aspergillus* enzyme towards this particular proline residue, BCM-7 as well as all BCM-7 related molecules are effectively destroyed by incubation with this enzyme because the Tyr-Pro-Phe motif is cleaved by the enzyme. Moreover, BCM-7 molecules derived from A1 as well as from A2 beta-caseins are inactivated by incubation with the *Aspergillus* proline specific endoprotease.

The advantage of a true proline specific endoprotease is that the proline specific endoprotease can start hydrolysing proline rich sequences immediately upon contacting the enzyme with the protein. Prolyl oligopeptidases can become active only after a significant pre-degradation of the gluten or casein molecules by other, for example gastrointestinal endoproteases. In view of the required extensive degradation and the limited time available before the food enters the small intestine, a true proline specific endoprotease has significant application advantages over the known oligopeptidases. Another advantage of a true proline-specific endoprotease is that it can be industrially used to reduce the level of toxic proline rich peptides in gluten without a total destruction of the gluten structure. For example extruding a wheat gluten paste together with the *Aspergillus* derived enzyme will yield a product with some residual textural properties but with a strongly reduced level of toxic proline rich peptides. To achieve the same reduction of toxic proline rich peptides with a prolyl oligopeptidase an almost total pre-hydrolysis with other proteases would be required to achieve the desired peptide lengths below 30 amino acid residues. Needless to say that this will result in a complete loss of all relevant physico-chemical properties of the gluten i.e. in a loss of dough consistency and precluding the baking of loafs with an acceptable shape and volume. Di Cagno et al (Appl. Environ. Microbiol., Vol 70(2)1088-1096, 2004) report the making of a sourdough bread that is well tolerated by celiac sprue patients. In their approach the level of toxic proline rich epitopes was minimised by using a dough prepared with a high proportion of nontoxic flours and fermenting this with selected *lactobacilli* for a 24 hours period. Although their results are certainly of scientific interest, it is obvious that in an industrial environment fermentation periods as long as 24 hours are economically not feasible. Furthermore their high proportion of nontoxic flours implies that it there will be a shortage of "regular" gluten so that the volume of the final loaf will be limited. Therefore it would be advantageous to avail of an economic method enabling the production of 100% wheat bread using existing industrial procedures but with limited levels of toxic proline rich peptides. Such breads can become an important component of diets aimed at reducing the daily intake of toxic peptides. Consumer groups for which such a diet is of special relevance includes infants, youngsters suffering from IBS, elderly people and individuals suffering from diseases and symptoms as described. Although for celiac patients a daily intake of less than 50 milligrams gluten is considered safe, any diet containing significantly less toxic proline rich peptides than present in the average Western consumption of 13 grams gluten per day is likely to be beneficial for the above mentioned consumer groups.

Collectively these considerations indicate novel and considerable advantages for the *A. niger* derived enzyme over the enzymes mentioned in the prior art. Compositions containing the enzymes according to the invention are advantageously used to reduce or delay gluten sensitisation or the phenomena of a disturbed opioid metabolism or the phenomena of IBS. Such compositions can be applied as a digestive aid to achieve a gastrointestinal in situ reduction of the toxic proline rich peptides. Alternatively such compositions can be applied as a processing aid to produce protein hydrolysates without such toxic proline rich peptides. Within the field of protein hydrolysates the brewing of beer provides a special case in which the application of the *A. niger* derived, low pH, proline specific endoprotease offers a surprising number of advantages. WO 02/046381 teaches that a prolyl specific endoprotease applied during either the beer mashing step or before beer filtration or before beer lagering will reduce the formation of beer haze. Our present data illustrate that an adequate incubation with the low pH enzyme will also reduce the level of cereal derived toxic proline-rich proline rich peptides. Surprisingly we have found that the treatment of beers or other beverages containing cereal proteins with the proline-specific endoprotease will not only result in reduced haze levels but will also lead to products that will be safe for people suffering from celiac disease.

Example 1 of the present application shows the acidic pH optimum and an ideal temperature optimum of the *Aspergillus* derived proline specific endoprotease. In Examples 2 and 3 we show that the proline specific endoprotease producible by *Aspergillus niger* is a true proline specific endoprotease that can cleave large, intact proteins with the same efficiency as smaller peptides or polypeptides. In fact our data indicate that the *Aspergillus* enzyme is a new member of the S28 family rather than the S9 family to which the known oligopeptidases belong (N. D. Rawlings and A. J. Barrett, Methods in Enzymology, Vol. 244, pp 1961, 1994; N. D. Rawlings and A. J. Barrett, Biochimica & Biophysica Acta 1298(1996) 1-3). We have found that, in contrast with the known prolyl oligopeptidases, the *Aspergillus* derived prolyl endoprotease is active under the acidic conditions in the stomach and shows high efficiencies towards the hydrolysis of large proline rich protein fragments and polypeptides. Such high efficiencies are illustrated in Examples 4, 5 and 6. In Example 4 we demonstrate that during the production of milk protein hydrolysates with Alcalase, an aggressive broad spectrum protease frequently used in the production of protein hydrolysates, several peptides incorporating BCM-7 sequences survive the hydrolysis process. However, these peptides rapidly disappear upon an incubation under acid conditions with the *Aspergillus* derived prolyl endoprotease. The data provided in Example 5 reveal the surprising fact that the *Aspergillus* enzyme cleaves only one of the four proline residues available in beta-A2 casein derived BCM-7 molecule. This indicates that the incubation of a proline rich substrate with any proline-specific protease does not automatically imply the cleavage of all peptide bonds involving a proline residue, not even under conditions of a dramatically increased enzyme/substrate ratio. In Example 6 we demonstrate the efficacy of the *Aspergillus* derived prolyl endoprotease towards the gliadin derived 33-mer claimed to be a major epitope in celiac patients. Although again the broad spectrum Alcalase cannot cleave this molecule, neither under alkaline nor under acid conditions, the *Aspergillus* derived enzyme frequently cleaves the molecule under acid conditions generating 99.5% peptides with a maximum length of 6 amino acid residues. So, despite its high efficacy towards proline rich peptides under acid conditions, even the *Aspergillus* derived enzyme leaves at least 0.5% of a heptamer with the amino acid sequence YPQPQLP. As the sequence PYPQPQLPY is a known celiac patient-specific T cell epitope, this finding illustrates that for suboptimal proline specific enzymes such as the known proline specific oligopeptidases including the enzyme derived from *Flavobacterum meningosepticum* a realistic in vivo application to prevent the formation of toxic peptides from gluten molecules will proof to be impossible. The latter conclusion is confirmed by the experiments shown in Examples 7 and 8. In Example 7 we compare the activity profiles of the *A. niger* derived proline specific endoprotease with the *F. meningosepticum* derived proline specific oligopeptidase between pH 2-12. Whereas the *A. niger* derived enzyme shows activity between pH 2.5 and 7.0, the *F. meningosepticum* enzyme needs a pH above 5.0 to become active. In Example 8 we mimic the situation in the stomach by exposing both proline specific enzymes to low pH conditions in the absence and presence of the gastric enzyme pepsin. Subsequent activity measurements under pH conditions optimal for the individual enzyme show that the *F. meningosepticum* enzyme cannot survive pH2 or pH 3 conditions. In the presence of pepsin the *F. meningosepticum* enzyme is already irrecoverably damaged at pH 4. In contrast, the *A. niger* derived enzyme survives pH conditions as low as pH 2 and even in the presence of pepsin hereby emphasizing its value for hydrolysing toxic peptides in the stomach. In Example 9 we illustrate that the *A. niger* derived enzyme can cleave a large number of known HLA-DQ2 gluten epitopes. Interestingly the positions of observed cleavage sites predict that all T-cell epitopes as known from the literature are destroyed. In Example 10 we recover gluten epitopes from 100% malt beer and 100% wheat bread and demonstrate that we can detect these epitopes in an antibody assay. In Example 11 we demonstrate that beer produced by incorporating the *A. niger* derived enzyme into the production process results in appreciably lowered levels of gluten epitopes. In Example 12 we show that a similar effect can be obtained by incorporating the enzyme into a wheat dough to produce a Dutch tin bread with lowered levels of gluten epitopes.

Gluten is a non-water soluble compound with a complex three dimensional structure. These properties in combination with its proline rich amino acid composition make the gluten molecules resistant to gastric and intestinal proteolysis. As none of the natural proteolytic activities secreted into the gastrointestinal lumen is capable of cleaving peptide bonds involving proline, the use of synergistic exogeneous proline specific enzymes makes sense. However, persons suffering from celiac disease can be extremely sensitive towards the many epitopes that are present in gluten. According to the present invention the effect of the natural digestive proteases can be improved with the *Aspergillus* derived prolyl endoprotease, and even further enhancement of the hydrolytic capacity of this proteolytic mixture is disclosed herein.

It is well known that peptide bonds involving negatively charged residues such as Glu (E) and Asp (D) form poor substrates for proteases. Also the natural gastrointestinal proteolytic enzymes cannot cope with these residues as evidenced by the isolation of the gastric and pancreatic protease resistant peptide WQIPEQSR (SEQ ID NO:6) from gliadin (cf. Shan et al). The latter publication also makes clear that the ubiquitously present glutamine residues (Q) in gluten can be deamidated to glutamate residues (E) by tissue transglutaminase. Unfortunately this regiospecific deamidation of gliadin peptides further increases their immunogenic potential. Against this background we have been able to create an effective enzyme combination existing of an *Aspergillus* derived proline specific endoprotease with an endoprotease to prevent the formation of proline rich toxic proline rich peptides. According to the present invention glutamate-specific endoproteases (EC3.4.21.19) can be used, for example those glutamate-specific endoproteases that are over secreted by a number of food-grade microorganisms such as *Bacillus* and *Streptomyces*. These enzymes can be produced in an economic and food-grade way. Enzymes which have a safe passage through the stomach, with respect to their enzymatic activity are preferred. In general those enzymes will have an acidic or neutral pH optimum. In combination with the *Aspergillus* derived prolyl endoprotease, this category of glutamate-specific endoproteases is considered useful in the production of protein hydrolysates with low levels of toxic proline rich peptides.

Quite surprisingly our present research demonstrates that apart from the glutamate-specific endoproteases other endoproteases exist that have a synergistic effect on incubations with the proline specific endoprotease from *Aspergillus*. We conclude that endoproteases (EC 3.4.21-99) capable of cleaving between the amino acid residues Q (glutamine) and L (leucine) are advantageously combined with the proline specific endopeptidase from *Aspergillus*. Especially endoproteases that have pH optima below pH 5.0 and prefer either glutamine or leucine residues in the P1 or in the P1' position of the substrate such as the aspergillopepsins (EC 3.4.23.18 and 19) and the mucorpepsins (EC 3.4.23.23) are advantageously used.

One application of the enzymes according to the invention is their use as a digestive aid. In this application the compositions of the present invention are preferably administered orally, but may also be administered via other direct routes. The compositions are typically administered to human beings but may also be administered to animals, preferably mammals, to relief the symptoms typical for an increased gluten sensitivity or a disturbed casein or gluten metabolism or IBS. In their application as digestive aid the enzymes according to the invention may be formulated as a dry powder in, for example, a pill, a tablet, a granule, a sachet or a capsule. Alternatively the enzymes according to the invention may be formulated as a liquid in, for example, a syrup or a capsule or may be incorporated into a food product with a water activity (Aw) below 0.85. The compositions used in the various formulations and containing the enzymes according to the invention may also incorporate at least one compound of the group consisting of a physiologically acceptable carrier, adjuvant, excipient, stabiliser, buffer and diluant which terms are used in their ordinary sense to indicate substances that assist in the packaging, delivery, absorption, stabilisation, or, in the case of an adjuvant, enhancing the physiological effect of the enzymes. The relevant background on the various compounds that can be used in combination with the enzymes according to the invention in a powdered form can be found in "Pharmaceutical Dosage Forms", second edition, Volumes 1, 2 and 3, ISBN 0-8247-8044-2 Marcel Dekker, Inc. Although the enzymes according to the invention formulated as a dry powder can be stored for rather long periods, contact with moisture or humid air should be avoided by choosing suitable packaging such as for example an aluminium blister. If formulated in a liquid form, the compounds used for stabilising the enzyme activity and microbial preservation play an important role. The stabilisation of enzyme activity may require lowered water activities as can be obtained by the use of polyols such as glycerol or various sugars. Moreover, divalent cations such as Ca2+ or Mg 2+ are known for their stabilising effects as well as reducing agents such as sulphur containing amino acids and phenolic compounds such as BHT or propyl gallate. Food grade microbial preservation may be achieved using well known combinations of low pH conditions or low water activities with sorbate or benzoate or parabenes. Furthermore food grade thickeners such as a hydrocolloid may be required. A relatively new oral application form is the use of gelatin capsule containing a liquid. In this application the liquid is typically an oil or a poly ethylene glycol or a lecithin in which the dried enzymes according to the invention can be suspended. Examples of tablet formulations with an improved enzyme stability are provided in US2002/0136800.

MATERIALS AND METHODS

Figure 1:
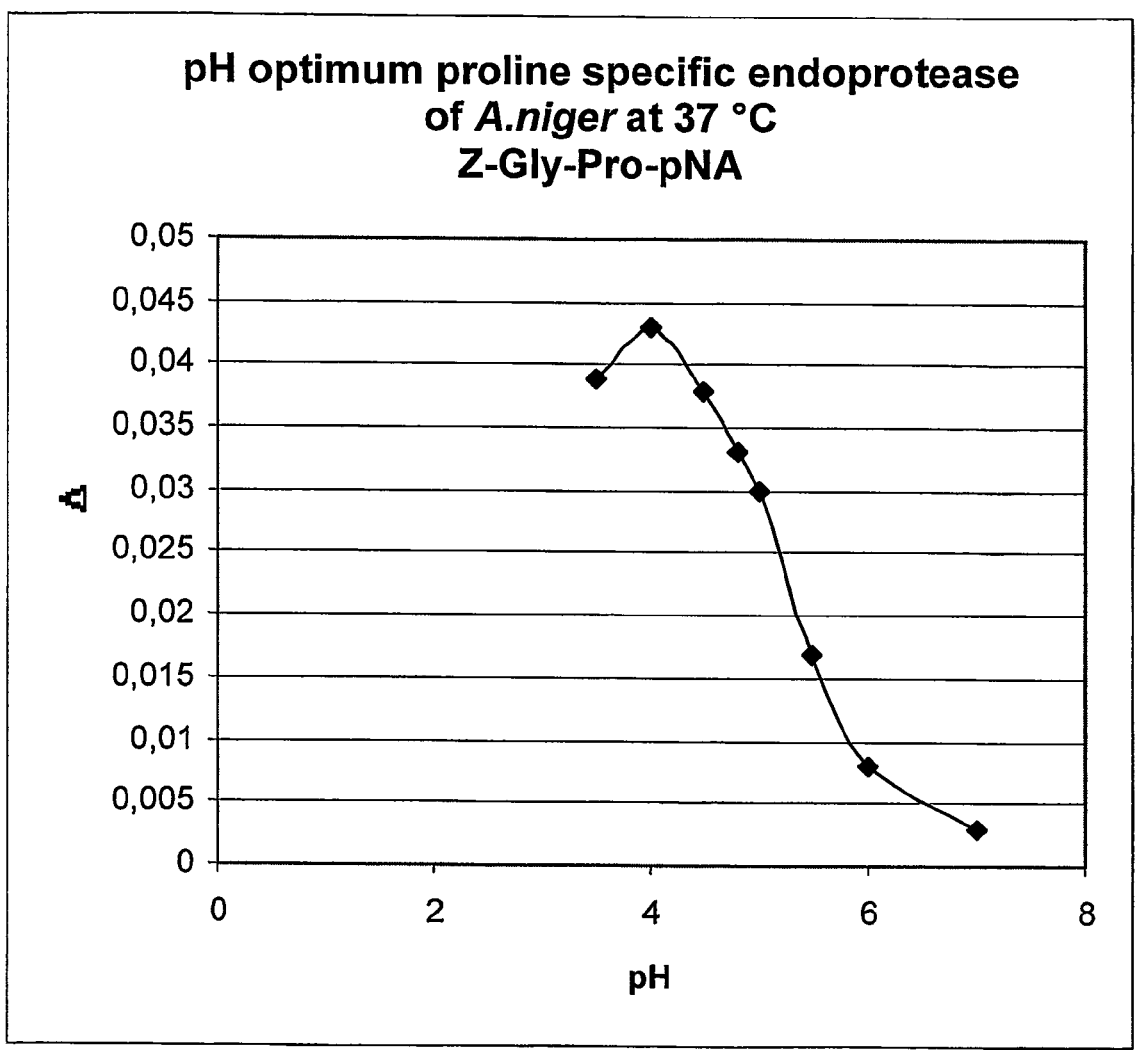
FIG. 1: A graphic representation of the pH optimum of the *A. niger* derived proline specific endoprotease using the synthetic peptide Z-Gly-Pro-pNA as the substrate (cf Example 1).

Materials.

The following enzymes were obtained from Sigma: amyloglucosidase from *Aspergillus niger*, 300 U/ml, Sigma A-7095; pepsin from porcine stomach mucosa, 2331 U/mg, Sigma P-7012; transglutaminase from Guinea pig, Sigma T-5398. Trypsin solution 2.5% was obtained from Gibco (BRL 25090-028) and Sep-Pak Plus tC18 cartridges, Waters No. 036810 from Waters. Alcalase® AF 2.4 L having an activity of 2.6 AU(A) (Anson Unit Alcalase) Units/gram product was obtained from Novozymes A/S (Bagsvaerd, Denmark). According to Novozymes the details of this activity measurement can be found in Novozymes Analytical Method LUNA#2003-32153-01/SOPNo.:EB-SM-0218.02/02).

Synthetic peptides were obtained from Pepscan Systems B.V. (Lelystad, The Netherlands). Chromogenic peptide substrates were obtained either from Pepscan Systems or from Bachem, Switserland.

Proline-Specific Endoprotease from *A. niger.*

Overproduction and chromatographic purification of the proline specific endoprotease from *Aspergillus niger* was accomplished as described in WO 02/45524. The activity of the enzyme (1 unit/10 mg of protein) was tested on the synthetic peptide Z-Gly-Pro-pNA at 37 degrees C. in a citrate/disodium phosphate buffer pH 4.6. The reaction product was monitored spectrophotometrically at 405 nM. The activity of the commercial prolyl oligopeptidase enzyme (as purchased from ICN Biomedicals/MP Biomedicals, Aurora, Ohio, US) was 35 units per mg product and was tested on Z-Gly-Pro-pNA at 30 degrees C. in a pH 7.0 buffer. The reaction product was monitored spectrophotometrically at 405 nM. For both enzymes a unit is defined as the quantity of enzyme that provokes the release of 1 mmol of p-nitroanilide per minute under the conditions as specified. LC/MS analysis.

HPLC using an ion trap mass spectrometer (Thermo Electront®, Breda, the Netherlands) coupled to a P4000 pump (Thermoquest®, Breda, the Netherlands) was used in characterising the enzymatic protein hydrolysates produced by the inventive enzyme mixture. The peptides were separated using a PEPMAP C18 300A (MIC-15-03-C18-PM, LC Packings, Amsterdam, The Netherlands) column in combination with a gradient of 0.1% formic acid in Milli Q water (Millipore, Bedford, Mass., USA; Solution A) and 0.1% formic acid in acetonitrile (Solution B) for elution. The gradient started at 95% of Solution A and increased to 40% of solution B in 140 minutes and was kept at the latter ratio for another 5 minutes. The injection volume used was 50 microliters, the flow rate was 50 microliter per minute and the column temperature was maintained at 30° C. The protein concentration of the injected sample was approximately 50 micrograms/milliliter.

Detailed information on the individual peptides was obtained by using the "scan dependent" MS/MS algorithm, which is a characteristic algorithm for an ion trap mass spectrometer.

Full scan analysis was followed by zoom scan analysis for the determination of the charge state of the most intense ion in the full scan mass range. Subsequent MS/MS analysis of the latter ion resulted in partial peptide sequence information, which could be used for data base searching using the SEQUEST application from Xcalibur Bioworks (Thermoquest®, Breda, The Netherlands). Data banks used were extracted from the OWL.fasta databank, available at the NCBI (National Centre for Biotechnology informatics), containing the proteins of interest for the application used. In those experiments in which well characterized protein substrates such as whey proteins or caseins were measured, the precision of the analysis technique was increased by omitting those MS/MS spectra with a sequence fit of less than 50%.

Angiotensin (M=1295.6) was used to tune for optimal sensitivity in MS mode and for optimal fragmentation in MS/MS mode, performing constant infusion of 60 microg/ml, resulting in mainly doubly and triply charged species in MS mode, and an optimal collision energy of about 35% in MS/MS mode.

MALDI-TOF

MALDI-TOF was performed using a Voyager De-Pro (Applied Biosystems) mass spectrometer. After mixing with the appropriate matrix, peptide samples were measured in a linear mode. Masses found via MassLynx software, were sequenced by Post Source Decay (PSD) to confirm the amino acid sequence of the peptides proposed.

Quantification of Gluten Peptides in Food Samples.

Monoclonal antibodies specific for T cell stimulatory alpha-gliadin, gamma-gliadin and LMW-glutenin peptides are available and were incorporated in a competition assay for the detection of these peptides in food samples (E. H. A. Spaenij-Dekking et al., GUT, 53: 1267-1273 (2004).

Antibody Based Assays.

For the generation of an antibody-based assay, monoclonal antibodies were raised in Balb C mice against known T cell stimulatory alpha-, gamma-gliadin and a LMW glutenin peptide. After fusion of the spleens of the mice with a mouse myeloma cell line, antibody-producing hybridomas were obtained. These were cloned by limiting dilution and the monoclonal antibodies secreted by these cells were tested for their use in a monoclonal antibodies competition assay. For each of the specificities one or two suitable monoclonal antibodies were selected and the epitopes recognized by the different monoclonal antibodies were determined (see Table underneath).

| specificity | T cell epitope | Antibody epitope |
|---|---|---|
| α-gliadin (Glia-alpha2/9) | QLQPFPQPQLPY | QPFPQPQ |
| γ-gliadin (Glia-gamma1) | QPQQPQQSPFQQQRPF | QQRPFI |
| LMW glutenin (Glt-156) | QPPFSQQQQSPFSQ | QSPFS or PPFSQQ |

In the above Table, QLQPFPQPQLPY is SEQ ID NO:7, QPFPQPQ is SEQ ID NO: 8, QPQQPQQSPFQQQRPF is SEQ ID NO:9, QQRPFI is SEQ ID NO:10, QPPFSQQQQSPFSQ is SEQ ID NO:11, QSPFS is SEQ ID NO:12, PPFSQQ is SEQ ID NO:13.

EXAMPLES

Example 1

The pH and Temperature Optima of the Proline Specific Endoprotease as Obtained from *A. niger*

The *A. niger* derived proline specific endoprotease was overexpressed in an *A. niger* host, isolated and chromatographically purified using the materials and methods described in WO 02/45524. To establish the pH optimum of the thus obtained enzyme, buffers with different pH values were prepared. Buffers of pH 4.0-4.5-4.8-5.0-5.5 and 6.0 were made using 0.05 mol/l Na-acetate and 0.02 M CaCl2; buffers of pH 7.0 and 8.0 were made using 0.05 M Tris/HCl buffers containing 0.02 M CaCl2. The pH values were adjusted using acetic acid and HCl respectively. The chromogenic synthetic peptide Z-Gly-Pro-pNA was used as the substrate. The buffer solution, the substrate solution and the prolyl endoprotease pre-dilution (in an activity of 0.1 U/mL), were heated to exactly 37.0° C. in a waterbath. After mixing the reaction was followed spectrophotometrically at 405 nm at 37.0° C. for 3.5 min, measuring every 0.5 min. From the results shown in FIG. 1 it is clear that the *A. niger* derived proline specific endoprotease has a pH optimum around 4.

Also the temperature optimum of the prolyl endoprotease was established. To that end the purified enzyme preparation was incubated in 0.1 mol/l Na-acetate containing 0.02 mol/l CaCl2 at pH 5.0 for 2 hours at different temperatures using Caseine Resorufine (Roche version 3) as the substrate and enzyme activity was quantified by measuring at 574 nm. According to the results obtained the proline specific endoprotease from *A. niger* has a temperature optimum around 50 degrees C.

The very acidic pH optimum strongly suggests that the *A. niger* derived proline specific endoprotease has ideal properties for industrial application as well as for oral consumption as it will be optimally active under the acidic conditions preferred for industrial application and the conditions prevailing in the stomach and the early part of the small intestine. Also the temperature optimum of the enzyme makes the enzyme ideally suitable for both applications.

Example 2

The Enzyme as Obtained from *A. niger* Represents a New Class of Proline Specific Enzymes From the entire coding sequence of the *A. niger* derived proline specific endoprotease as provided in WO 02/45524 a protein sequence of 526 amino acids can be determined. The novelty of the enzyme was confirmed by BLAST searches of databases such as SwissProt, PIR and trEMBL. To our surprise, no clear homology could be detected between the *A. niger* enzyme and the known prolyl oligopeptidases. Closer inspection of the amino acid sequence, however, revealed low but significant homology to Pro-X carboxypeptidases (EC3.4.16.2), dipeptidyl aminopeptidases I (EC3.4.14.2), and thymus specific serine protease. All of these enzymes have been assigned to family S28 of serine peptidases. Also the GxSYxG configuration around the active site serine is conserved between these enzymes and the *A. niger* derived endoprotease. Additionally, members of family S28 have an acidic pH optimum, have specificity for cleaving at the carboxy-terminal side of proline residues and are synthesized with a signal sequence and propeptide just like the *A. niger* derived proline specific endoprotease. Also the size of the *A. niger* enzyme is similar to those the members of family S28. Therefore, the *A. niger* proline specific endoprotease appears to be a member of family S28 of serine proteases rather than the S9 family into which most cytosolic prolyl oligopeptidases including the enzyme obtained from *Flavobacterium meningosepticum* have been grouped. On the basis of these structural and physiological features we have concluded that the *A. niger* enzyme belongs to the S28 rather than the S9 family of serine proteases. An additional feature that discriminates the *A. niger* derived enzyme from the prolyl oligopeptidases belonging to the S9 family is the fact that, unlike the cytosolic prolyl endoproteases belonging to the latter family, the newly identified *A. niger* enzyme is secreted into the growth medium. So far only the basidiomycete *Agaricus bisporus* (Sattar et al; J. Biochem. 107, 256-261 (1990)) and the non-related ascomycete *Aspergillus niger* (WO 02/45524) have been shown to produce an extracellular prolyl endopeptidase. However, the enzyme obtained from the basidiomycete will not survive pH values below 5 and is therefore far less suitable for industrial application as well as for oral consumption.

This is the first report on the isolation and characterization of a member of family S28 from a lower eukaryote.

Example 3

The *A. niger* Derived Proline Specific Endoprotease can Hydrolyse Large Proteins as Well as Small Peptides and is Thus a True Endoprotease Owing to a specific structural feature, prolyl oligopeptidases belonging to the S9 family cannot digest peptides larger than 30 amino acids. This limitation is an obvious disadvantage for an enzyme, which is meant to hydrolyse as quickly and as efficiently as possible all potential proline rich toxic proline rich peptides. To see if the *A. niger* derived proline specific endoprotease exhibits the same limitations with respect to the size of the substrate molecule, we have incubated the chromatographically purified prolyl endopeptidase from *A. niger* with a small synthetic peptide and with the large ovalbumine molecule and have analysed the hydrolysis products formed by SDS-PAGE. The synthetic peptide used was a 27-mer of the sequence NH2-FRASDNDRVID-PGKVETLTIRRLHIPR-COOH (SEQ ID NO:14) and was a gift of the Pepscan company (Lelystad, The Netherlands). As shown by its amino acid sequence, this peptide contains 2 proline residues, one in the middle and one near the very end of the peptide. The intact ovalbumine molecule (Pierce Imject, vials containing 20 mg freeze dried material) consists of 385 amino acids with a molecular weight of 42 750 Da. This molecule contains 14 proline residues one of which is located at the ultimate C-terminal end of the molecule and cannot be cleaved by a proline specific endoprotease. Ovalbumin and the oligopeptide were separately incubated at 50° C. with the purified *A niger* derived proline specific endoprotease. At several time intervals samples were taken which were then analysed using SDS-PAGE.

A chromatographically purified *A. niger* derived proline specific endoprotease with an activity of 4.5 units/ml was diluted 100-fold with 0.1 M acetate buffer pH 4 containing 20 mM CaCl2. The ovalbumine was dissolved in acetate buffer pH 4 to a concentration of 1 mg/ml (22 µM). The 27-mer was dissolved in the same buffer to reach a concentration of 0.48 mg/ml (152 µM). The molarity of the ovalbumine and the 27-mer solution was chosen in such a way that both solutions contained the same molarity in cleavable proline residues. Ovalbumine contains 13 potential proline cleavage sites, whereas the 27-mer peptide has only two. Of both substrate solutions 0.5 ml was incubated with 10 µl (0.45 milliU) of the enzyme solution in an Eppendorf thermomixer at 50° C. At several time intervals 10 µl samples were withdrawn from the incubation mixture and kept at 20° C. until SDS-PAGE. All materials used for SDS-PAGE and staining were purchased from Invitrogen. Samples were prepared using LDS buffer according to manufacturers instructions and separated on 12% Bis-Tris gels using MES-SDS buffer system according to manufacturers instructions. Staining was performed using Simply Blue Safe Stain (Collodial Coomassie G250).

Figure 2:
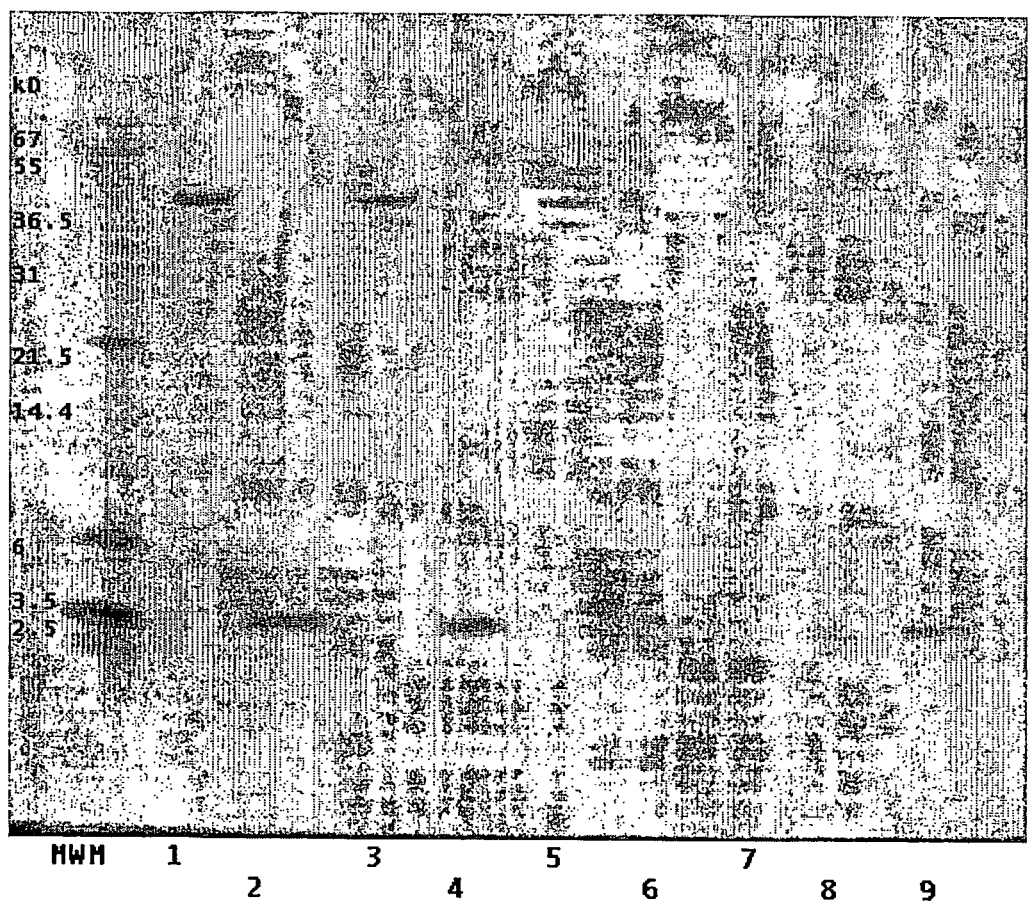
FIG. 2: SDS-PAGE of intact ovalbumine and a synthetic 27-mer peptide after incubation with a chromatographically purified *A. niger* derived proline specific endoprotease (cf Example 3)

As can be seen in FIG. 2 ovalbumine is cleaved by the *Aspergillus* derived enzyme into a discrete band of about 35 to 36 kD in the first 4.75 hours of incubation (lane 3). Prolonged incubation periods result in further breakdown to smaller products of various molecular weights (lane 7).

The 27-mer peptide is also broken down, as judged by the more faint bands in lanes 4, 6 and 8 as compared to lane 2. The very small molecular weight shift of the product (compare lanes 9 and 8) is most likely due to cleaving of the arginine residue at the carboxylic end of the peptide. The difference is about 200D (measured using AlphaImager 3.3d software on an AlphaImager 2000 system) and arginine has a MW of 174. This small molecular weight shift is probably the first step in the breakdown of the peptide.

The further decay of the product can only be seen by the decrease in intensity of the band on the SDS gel. The products of further decay are not visible, as in gel staining of components with a MW of about 1000 is not possible with Coomassie Brillant Blue.

From this experiment it can be concluded that, unlike the known prolyl oligopeptidases belonging to the S9 family, the *A. niger* derived proline specific endoprotease has no specific preference for cleaving small sized peptides over much larger proteins. As such the *A. niger* derived enzyme represents a true endoprotease and a preferred enzyme to cleave potential toxic proline rich proline rich peptides.

Example 4

Beta-Casomorphins in Hydrolysates Formed after Incubation with Alcalase and a Combination of Alcalase Plus Proline Specific Endoprotease from *A. niger*

In analogy with the formation of protease-resistant beta-casomorphins during gastro-intestinal proteolysis, we wondered whether during the industrial production of milk protein hydrolysates a similar accumulation of BCM-7 related peptide fragments would occur. To that end we incubated A2 beta-casein isolated from bovine milk with the industrially frequently used subtilisin Alcalase and with Alcalase plus the proline specific endoprotease from *A. niger*. Using LC/MS/MS analysis the peptides thus formed were analysed.

Bovine milk contains almost 10 grams of beta-caseine per kg of milk representing 28% of all protein present. To facilitate the analysis of BCM-7 related amino acid sequences, in this experiment we used a concentrated preparation (from Sigma) containing a minimum of 90% (A2)beta-casein. The latter product was dissolved in water in a concentration of 20 grams per liter after which the pH was adjusted to 8 using NaOH and Alcalase was added in an amount of 800 microliter of enzyme concentrate per liter of casein solution. Incubation was carried out for 2 hours at 60° C. Then the pH of the solution was lowered till 4.5 using citric acid. The solution was then split into two parts: one part was heated for 5 minutes at 90° C. to inactivate the Alcalase and to the other part the *A. niger* derived proline specific endoprotease was added to obtain an enzyme concentration of 1 unit per gram of casein present (see Materials &Methods section for unit definition). Incubation with the *A. niger* derived proline specific endoprotease was continued for 16 hours at 55° C. followed by another heat treatment to inactivate the proline specific endoprotease. Finally two samples with an estimated beta-casein concentration of 20 mg/ml were supplied for LC/MS/MS analysis. The two samples were centrifuged for 10 minutes at 13000 rpm and diluted 20 times in Milli Q prior to LC/MS/MS analysis. LC/MS/MS analysis was carried out as described in the Materials &Methods section.

Apart from the BCM-7 sequence Tyr-Pro-Phe-Pro-Gly-Pro-Ile (SEQ ID NO:15) at amino acid positions 60-66 of the beta-casein molecule, the smaller fragments like Tyr-Pro-Phe-Pro (beta-casomorphin (1-4)) (SEQ ID NO:16 and Tyr-Pro-Phe-Pro-Gly (beta-casomorphin (1-5)) (SEQ ID NO:17) at amino acid positions 60-63 and 60-64 respectively as well as all larger peptides up to a chain 30 length of 11 amino acids (at amino acid positions 60-70) display at least some degree of opioid activity. The tripeptide Tyr-Pro-Phe at position 60-62 has been reported to have no opioid activity.

For the peptide identification direct LC/MS/MS of the protonated molecules was used. The protonated masses of the possibly relevant peptides are provided in Table 1. All spectra were obtained with a collision amplitude of 35% and a peak width of 3 Da. All experimental data are compared with the theoretical fragmentation pattern based on the so-called B and Y ions. This is the process normally performed using automatic data processing.

TABLE 1

Peptide masses analyzed in LC/MS/MS mode.

| Peptide amino acid sequence | m/z |
|---|---|
| YPFPGPI | 790.4 |
| FPGPIPNS | 828.4 |
| YPFPGPIP | 887.5 |
| VYPFPGPI | 889.5 |
| VYPFPGPIP | 986.5 |
| LVYPFPGPI | 1002.5 |
| YPFPGPIPNS | 1088.5 |
| LVYPFPGPIP | 1099.6 |
| VYPFPGPIPN | 1100.6 |
| VYPFPGPIPNS | 1187.6 |
| YPFPGPIPNSL | 1201.7 |
| LVYPFPGPIPN | 1213.6 |
| VYPFPGPIPNSL | 1300.7 |
| LVYPFPGPIPNSL | 1413.8 |

In Table 1, the sequence identification numbers of the listed sequences beginning with YPFPGPI and extending to LVYPFPGPIPNSL are SEQ ID NO:18 to SEQ ID NO:31, respectively.

Betacasomorphine amino acid sequences start with tyrosine (Y; residue nr 60 of the beta-casein peptide chain) and are given in bold. The m/z values represent the protonated molecules of other possibly relevant peptides. The detection of a proline residue at position 67 indicates that the substrate used represents A2 beta-casein.

The results obtained upon LC/MS/MS analysis of the beta-casein hydrolysates obtained after incubation with either Alcalase or Alcalase plus proline specific endoprotease are given in Table 2 and can be summarized as follows:

The exact beta-casomorphine sequences i.e. YPFPGPI (SEQ ID NO:18) and derivatives are not present in (A2) beta-casein treated with either Alcalase or the combination of Alcalase plus the proline specific endoprotease from *A. niger*.

However, two peptides containing the beta-casomorphin sequence are present in the Alcalase-treated sample i.e. LVYPFPGPIPN (SEQ ID NO:29) and VYPFPGPIPN (SEQ ID NO:26).

The intensity of these beta-casomorphin containing sequences are drastically reduced upon treatment with the proline specific endoprotease from *A. niger*.

TABLE 2

LC/MS/MS identification of peptides containing the beta-casomorphin (1-7) amino acid sequence

| Peptide amino acid sequence | m/z | Intensity after Alcalase treatment | Intensity after Alcalase prol.spec endoprotease treatment |
|---|---|---|---|
| YPFPGPI | 790.4 | – | – |
| FPGPIPNS | 828.4 | – | – |
| YPFPGPIP | 887.5 | – | – |
| VYPFPGPI | 889.5 | – | – |
| VYPFPGPIP | 986.5 | – | – |
| LVYPFPGPI | 1002.5 | – | – |
| YPFPGPIPNS | 1088.5 | – | – |
| LVYPFPGPIP | 1099.6 | – | – |
| VYPFPGPIPN | 1100.6 | $100 \cdot 10^7$ | $0.05 \cdot 10^7$ |
| VYPFPGPIPNS | 1187.6 | – | – |
| YPFPGPIPNSL | 1201.7 | – | – |
| LVYPFPGPIPN | 1213.6 | $3.5 \cdot 10^7$ | – |
| VYPFPGPIPNSL | 1300.7 | – | – |
| LVYPFPGPIPNSL | 1413.8 | – | – |

In Table 2, the sequence identification numbers of the listed sequences beginning with YPFPGPI and extending to LVYPFPGPIPNSL are SEQ ID NO:18 to SEQ ID NO:31, respectively.

The results clearly indicate that the combination of Alcalase plus the proline specific endoprotease from *A. niger* destroys all potential beta-casomorphin sequences with a high efficiency hereby offering a hydrolysate without potentially toxic proline rich proline rich sequences.

After a more precise search among the peptides formed we were able to demonstrate the presence of peptide VYP in the hydrolysate formed by the combination of the two enzymes. As this peptide could not be traced in the hydrolysate formed by using just Alcalase, this finding suggests cleavage C-terminal of the proline residue in position 61 of the beta-casein molecule by the *Aspergillus* derived enzyme.

Example 5

Peptides Formed Upon the Incubation of the Alcalase Formed Peptide VYPFPGPIPN (SEQ ID NO:26) with the Proline Specific Endoprotease from *A. niger*

As shown in Example 4, the hydrolysis of A2 beta-casein with a combination of Alcalase and the proline specific endoprotease from *A. niger* effectively removes all potential beta-casomorphin sequences. However, the complexity of the peptides generated did not allow us to establish at which position the *Aspergillus* derived enzyme cleaves the Alcalase formed peptide VYPFPGPIPN (SEQ ID NO:26). To that end a peptide with this specific sequence was synthesized and incubated with two concentrations of the proline specific endoprotease. Subsequent LC/MS/MS analysis of the peptides formed revealed the exact cleavage site of the enzyme.

The lyophilised 10-mer (Pepscan Systems; Lelystad, The Netherlands) was dissolved in a citrate-phosphate buffer pH 4.5 in a concntration of 2 mg/ml. To the solution proline specific endoprotease was added in concentrations of 1 and 10 units per gram of peptide. Incubation took place for 4 hours at 55 degrees C. after which a heat treatment of 5 minutes at 90 degrees C. was used to inactivate the enzyme. The two samples were then centrifuged for 10 minutes at 13000 rpm and diluted 20 times in Milli Q water prior to LC/MS and LC/MS/MS analysis. The samples were first analyzed in LC/MS mode to observe the decrease in intensity of the 10-mer using different amounts of enzyme and to observe which peptide masses appeared in the LC/MS ion chromatogram after enzymatic cleavage.

Then direct LC/MS/MS of the protonated molecules of the peptides found in the LC/MS runs was performed. All spectra were obtained with a collision amplitude of 35% and a peak width of 3 Da. All experimental data are compared with the theoretical fragmentation pattern based on the so-called B and Y ions. This is the process normally performed using automatic data processing for identification of peptides, polypeptides and proteins.

Treatment of the 10-mer VYPFPGPIPN (SEQ ID NO:26) (M=1099.5) with 1 unit/g of protein already resulted in total breakdown of the 10-mer into several peptides. The intensity of the protonated molecule, at m/z 1100.5, drops 3 orders of magnitude. Treatment of the 10 mer with 10 units/g did not result in further decrease of the intensity of the protonated molecule and also no other peptide masses were found. Upon enzymatic treatment with 1 unit/g 4 peptides were formed, with VYP (M=377.2), characterized by m/z 378.2 as the most abundant (almost 98%; see Table 3). All four peptides were analyzed in LC/MS/MS mode and found to be correct, based on the criteria described above. Table 3: Protonated peptide masses analyzed in LC/MS and LC/MS/MS mode of the 10-mer VYPFPGPIPN (SEQ ID NO:26) M=1099.5. The second column presents the m/z values of the protonated molecules, the third column the intensity of the protonated molecules observed in LC/MS mode, the fourth column the percentage based on peak area of the protonated molecule and the fifth column the position of the peptides found in the total amino acid sequence of the 10-mer. It should be emphasized that using peak areas of protonated molecules of peptides does not include the influence of differences in ionization efficiencies.

TABLE 3

Peptides formed upon the incubation of the BCM-7 related 10-mer VYPFPGPIPN (SEQ ID NO: 26) with the *A. niger* derived proline specific endoprotease.

| Peptide amino acid sequence | m/z | Intensity in LC/MS mode | Percentage (%) | Position in total aa sequence |
|---|---|---|---|---|
| VYP | 378.2 | $1 \cdot 10^8$ | 97.7 | 1-3 |
| VYPF | 525.3 | $3 \cdot 10^5$ | 0.3 | 1-4 |
| VYPFP | 622.4 | $2 \cdot 10^6$ | 2.0 | 1-5 |
| VYPFPGP | 776.4 | $3 \cdot 10^4$ | 0.03 | 1-7 |

In Table 3, VYPF is SEQ ID NO:32, VYPFP is SEQ ID NO: 33, VYPFPGP is SEQ ID NO:34.

However, it can be concluded that the proline specific endoprotease from *A. niger* cleaves almost exclusively at the C-terminal side of the proline at position 61 (position 3 for this particular decapeptide. The cleavage performance is not influenced by increasing enzyme/substrate ratios.

As all known beta-casomorhin molecules with opioid activity share the N-terminal sequence YPF, it is evident that the efficient cleavage of this sequence between P and F (i.e. carboxyterminal of the proline residue at position 61) by the proline specific endoprotease will effectively inactivate all BCM-7 and BCM-7 related peptides, be it from the A1 or from the A2 genetic variant of beta-casein.

The crucial role of the proline residue in position 61 in the interaction with the mu-receptor was also confirmed in a recent internet publication ("Sintesi e affinita ai recettori oppiodi di analoghi delle beta-casomorphine contenenti beta-omo amminoacidi" by the Dipartimento di Scienza degli Alimenti Universita di Napoli"Frederico II" Facolta di Agraria).

Example 6

Peptides Formed Upon the Incubation of the Gliadin Derived 33-Mer LQLQPFPQPQLPYPQPQLPYPQPQLPYPQPQPF (SEQ ID NO:35) with the Proline Specific Endoprotease from *A. niger*

Treatment of the gastric and pancreatic juices resistant gliadin derived 33-mer LQLQPF-PQPQLPYPQPQLPYPQPQLPYPQPQPF (SEQ ID NO:35) (M=3911) as described by Shan et al (Science, Vol 297, 27 Sep. 2002) with Alcalase at either pH 8 or pH 5 did not result in any cleavage of the molecule. However, similar to the situation with the beta casein derived 10-mer, incubation with 1 unit of the proline specific endoprotease from *A. niger* at pH 5 resulted in total breakdown of the molecule into several peptides. The intensity of the triple protonated 33-mer at m/z 1304.4, drops 3 orders of magnitude. No further decrease of the intensity of the protonated molecule and also no other peptide masses were observed upon treatment of the 33-mer with 10 enzyme units per gram of protein.

After enzymatic treatment about 6 main peptides and several minor peptides were formed, with a peptide characterized by m/z 565.2 as the most abundant. All 6 peptides were analyzed in LC/MS/MS mode and they all were found to contain proline at the C-terminus, confirming the enzyme's specificity. The major peptide formed is characterized by m/z 565.2 (sequence .QLP in table 4). Although the C-terminal sequence "LP" could be unambiguously demonstrated for this peptide, the identified mass can theoretically not be formed by endoproteolytic degradation of the 33-mer so that there remains some uncertainty regarding the exact N-terminal composition of the peptide. Most probably m/z 565.2 is the N-pyroglutamyl variant of QPQLP (SEQ ID NO:36) (M=581.3), although this was not further investigated.

```
Appearance of QPQLP (SEQ ID NO: 36):
                                   (SEQ ID NO: 35)
LQLQPFPQPQLPYPQPQLPYPQPQLPYPQPQPF Appearance of QPQLPYP (SEQ ID NO: 37):
                                   (SEQ ID NO: 35)
LQLQPFPQPQLPYPQPQLPYPQPQLPYPQPQPF.
```

The LC/MS/MS spectrum of the peptide with m/z 679 could be elucidated to be PQPQLP (SEQ ID NO:39). Despite the fact that the nature of the peptide with m/z 565.2 was not fully understood, the data obtained clearly demonstrate the preferential cleavage of the praline specific endoprotease from *Aspergillus* at the C-terminal side of the proline residues at positions 12, 19 and 26 (i.e. exclusively between the proline and the tyrosine residue) of this particular 33-mer. This cleavage pattern is not influenced by using higher enzyme/substrate ratios. In table 4 all relevant information is summarized. The first column specifies the derived peptide sequences, dots used (also in column 5) indicate that no exact starting position of the peptide could be given due to unexplained mass discrepancies. The second column presents the m/z values of the protonated molecules, the third column the intensity of the peptides observed in LC/MS mode, the fourth column the percentages based on peak area of the protonated molecule and the fifth column the position of the peptides identified in the total amino acid sequence.

TABLE 4

Peptides formed upon incubation of the gliadin derived 33-mer LQLQPFPQPQLPYPQ PQLPYPQPQLPYPQPQPF (SEQ ID NO: 35) with the proline specific endoprotease from *A. niger*.

| Peptide amino acid sequence | m/z | Intensity in LC/MS mode | Percentage | Positions in total aa sequence |
|---|---|---|---|---|
| ...YP | 523.2 | 1.9 107 | 5.2 | ..14, ..21, ..28 |
| YPQPQLP | 842.3 | 1.7 106 | 0.5 | 13-19,20-26 |
| QPQP | 468.2 | 3.4 107 | 9.3 | 29-32 |
| PQPQLP | 679.2 | 3.4 107 | 9.3 | 14-19,21-26 |
| ..QLP | 565.2 | 2.4 108 | 65.9 | ..12, ..19, ..26 |
| ...P | 599.2 | 3.5 107 | 9.6 | |

In Table 4, YPQPQLP is SEQ ID NO:37, QPQP is SEQ ID NO:38, PQPQLP is SEQ ID NO:39.

Cleavage of the 33-mer, claimed to be a major epitope in celiac patients, cannot be accomplished by gastric or pancreatic juices or by incubation with the aggressive broad spectrum protease Alcalase, neither under alkaline nor under acid conditions. Nevertheless our results indicate an efficient cleavage by the proline specific *A. niger* derived endoprotease under acid conditions. The latter cleavage takes place exclusively between the proline and the tyrosine residues of the molecule and generates 99.5% of peptides with no more than 6 amino acid residues long. So, despite its high efficacy towards proline rich peptides under acid conditions, even the *Aspergillus* derived enzyme leaves at least 0.5% of a heptamer with the amino acid sequence YPQPQLP (SEQ ID NO:40). As the sequence PYPQPQLPYSEQ ID NO:41) is a known celiac patient-specific T cell epitope, this finding emphasizes once more that for suboptimal proline specific enzymes with near neutral pH optima such as the known proline specific oligopeptidases and the enzyme derived from *Flavobacterium meningosepticum*, a realistic in vivo application to prevent the formation of toxic peptides from gluten molecules will proof to be impossible.

Example 7

The pH Activity Spectra of the *A. niger* Proline Specific Endoprotease and the Proline Specific Oligopeptidase from *F. meningosepticum*

As demonstrated in Example 1, the pH optimum of the *A. niger* derived proline specific endoprotease is about 4.2. In this first test very acidic pH values were not contemplated so that the behaviour of the enzyme at the pH extremes that can exist in the stomach is not completely clear. WO 03/068170 teaches that proline specific proteases such as the prolyl oligopeptidase from *Flavobacterium meningosepticum* or DPPIV from *Aspergillus fumigatus* or peptidyl dipeptidases from *Streptomyces* species present preferred candidates for the in situ degradation of toxic proline rich peptides. Typically all of the latter proteases feature near neutral pH optima that seem to exclude any hydrolytic activity in the stomach. To demonstrate the difference in pH optima that exist between the proline specific endoprotease according to the invention and the prior art enzymes, we compared the pH activity spectra of the *Aspergillus* derived endoprotease and the *Flavobacterium* derived oligopeptidase. The *Aspergillus* derived endoprotease was obtained as described in Example 1. The *Flavobacterium* derived oligopeptidase was purchased from ICN Biomedicals (35 units/mg; cat no. 32082; Ohio, US).

Figure 3:
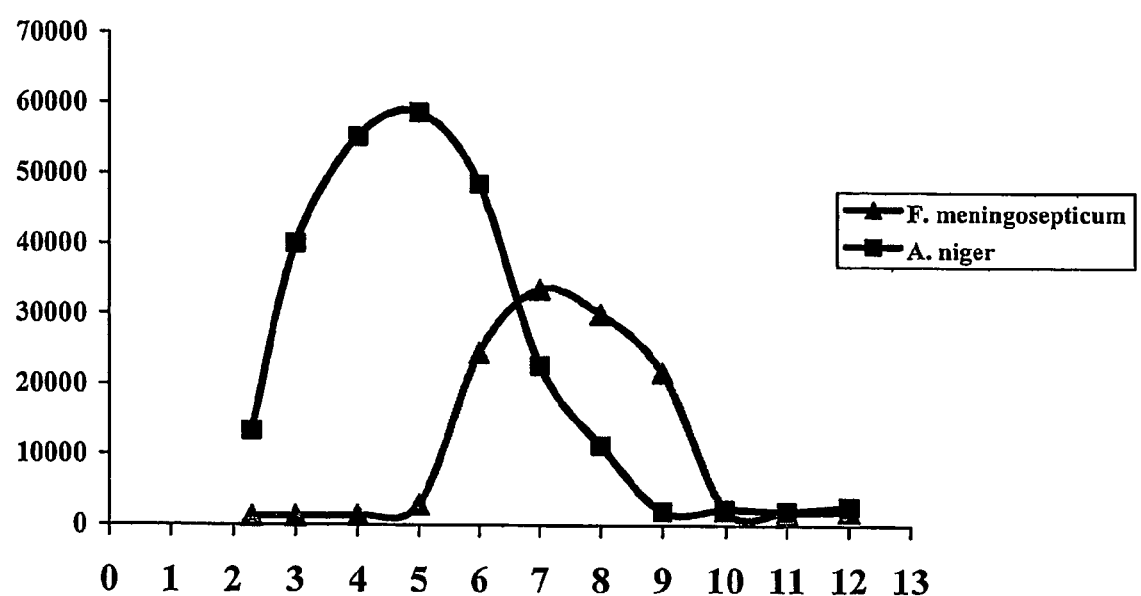
FIG. 3: A graphic representation of the pH optima of the *A. niger* and the *F. meningosepticum* derived proline specific endoprotease (cf Example 7).

To establish the pH activity spectra of the two enzymes, buffers with different pH values were prepared. Buffers ranging from pH 2.0 to 7.0 were prepared using 0.1 mol/l citrate, buffers ranging from pH 6.0 to 9.0 were prepared using 0.1 mol/l tris and buffers ranging from pH 8.0 to 12.0 were made using 0.2 mol/A glycine. The required pH values were adjusted using either HCl or NaOH. The chromogenic synthetic peptide Z-Gly-Pro-AMC (Bachem, Switserland) was used as the substrate for both enzymes. In each well (Costar no. 3631 plates) 85 uL of buffer, 10 uL of enzyme solution and 5 uL of the substrate (4 mM Z-Gly-Pro-AMC in 60% methanol) was introduced. Final concentration of the *A. niger* enzyme was 32 ug/ml (3.2 milli units/ml), final concentration of the *F. meningosepticum* enzyme was 0.21 ug/ml (7.4 milli units/ml). After mixing the reaction was allowed to proceed for 30 minutes at 37.0° C. after which the fluorescence was measured in a CytoFluor multi-well plate reader of PerSeptive Biosciences. The relative data as obtained are shown in FIG. 3. The data obtained under these slightly different testing conditions confirm the acidic pH optimum of the *A. niger* derived proline specific endoprotease as established in Example 1. The data show that the *A. niger* enzyme has approx 20% residual activity at pH 2.2 and 7.5. The data shown in FIG. 3 also confirm the published pH optimum of the *F. meningosepticum* around pH 7.0. More important in the context of the present patent application is that below pH 5.0 the *F. meningosepticum* enzyme has no activity.

These data show that in contrast with the *F. menigosepticum* enzyme, the *A. niger* derived proline specific endoprotease is ideally suited for deploying its full activity under the acid conditions prevailing in the stomach and part of the duodenum.

Example 8

Stabilities of the *A. niger* Proline Specific Endoprotease and the *F. meningosepticum* Proline Specific Oligopeptidase under Conditions as Present in the Stomach Prerequisite for a successful enzyme therapy is the efficient gastrointestinal degradation of toxic proline rich peptides before such peptides reach the distal part of the duodenum. This requires that the exogeneous enzyme to be used for the enzyme therapy is a proline specific protease that is active during the residence time of dietary protein in the stomach and optionally beyond the stomach. To compare the activities of the *A. niger* and the *F. meningosepticum* derived proline specific proteases under such "stomach-like" conditions, we assayed their residual activities after an incubation at 37 degrees C. for different time periods under different pH conditions and in the presence and absence of the gasric protease pepsin. Residual enzyme activities were assayed using a pH value and a chromogenic peptide optimal for the relevant enzyme i.e. a pH of 7.0 and the Z-Gly-Pro-pNA substrate for the *F. meningosepticum* enzyme and a pH of 4.0 and an Ala-Ala-Pro-pNA substrate for the *A. niger* enzyme. The *A. niger* enzyme as used shows high activity on Ala-Ala-Pro-pNA and some activity (less than 10% of its activity on Ala-Ala-Pro-pNA) on the Ala-Ala-Ala-pNA substrate. The *A. niger* enzyme as used shows no significant activity on other Ala-Ala-X-pNA substrates.

Citrate/HCl buffers of 0.2 mol/l were used for obtaining the required acid pH conditions. The dosage of the *A. niger* derived enzyme was 1.5 units/ml, the dosage of the *F. meningosepticum* enzyme (MP Biochemicals, Ohio, US) 3.3 units/ml (see Materials & Methods section for unit definitions). Pepsin (Sigma) was added in a concentration of 180 microgram/ml. Pepstatin (Sigma) was added after sampling in a concentration of 1.67 microgram/ml in order to inactivate the pepsin. Under these conditions pepstatin had no inhibitory effect on the two proline specific proteases. Residual activities of the two proline specific proteases were measured kinetically at 405 nm making use of the synthetic substrates Ala-Ala-Pro-pNA and Z-Gly-Pro-pNA respectively. To that end 200 μL substrate solution (2 mmol/l Z-Gly-Pro-pNA in a 0.05 mol/l phosphate buffer pH 70 or 1.5 mmol/l Ala-Ala-Pro-pNA in a 0.05 mol/l acetic acid buffer pH 4.0) was mixed with a 50 microliter (prediluted 10 to 100×) of the acid/pepsin treated sample in MTP wells. Absorbance was measured kinetically for 10 min at 405 nm at 30° C. making use of a TECAN Genios MTP Reader (Salzburg, Vienna).

The results depicted in Table 5 show that pH 4 represents the lower limit where the *F. meningosepticum* enzyme can survive. Please note that according to the data described in Example 7 the enzyme has no activity under these pH conditions. After 2 hours at pH 4.0 the enzyme shows approx 25% residual activity if tested under optimal conditions. However, as soon as pepsin is present, the enzyme is completely inactivated after 15 minutes at this pH. In contrast with these results are the data obtained with the *A. niger* enzyme. The latter enzyme maintains its full activity at pH values as low as pH 2 and even in combination with pepsin. These results strongly suggest that only enzymes with a pH optimum below 5.5 are likely to be active in the stomach so that known proline specific proteases belonging to the enzyme classes EC 3.4.21.26 (prolyl oligopeptidases), EC 3.4.14.5 (dipeptidyl-peptidase IV) and EC 3.4.15.1 (peptidyl-dipeptidase A) do not qualify for degrading proline rich peptides in the stomach.

TABLE 5

Residual enzyme activity of the *F. meningosepticum* oligopeptidase and the *A. niger* endoprotease after various incubation periods under stomach-like conditions

| Incubation Conditions | | Residual enzyme activity of the *F. meningosepticum* oligopeptidase after: | | | | Residual enzyme activity of the *A. niger* endoprotease after: | | | |
|---|---|---|---|---|---|---|---|---|---|
| pH | Pepsin present | 15 mins | 30 mins | 60 mins | 120 mins | 15 mins | 30 mins | 60 mins | 120 mins |
| 2 | No | − | − | − | − | + | + | + | + |
|   | Yes | − | − | − | − | + | + | + | + |
| 3 | Nos | − | − | − | − | + | + | + | + |
|   | Yes | − | − | − | − | + | + | + | + |

TABLE 5-continued

Residual enzyme activity of the *F. meningosepticum* oligopeptidase and the *A. niger* endoprotease after various incubation periods under stomach-like conditions

| Incubation Conditions | | Residual enzyme activity of the *F. meningosepticum* oligopeptidase after: | | | | Residual enzyme activity of the *A. niger* endoprotease after: | | | |
|---|---|---|---|---|---|---|---|---|---|
| pH | Pepsin present | 15 mins | 30 mins | 60 mins | 120 mins | 15 mins | 30 mins | 60 mins | 120 mins |
| 4 | No | + | + | + | +/− | + | + | + | + |
| | Yes | − | − | − | − | + | + | + | + |

+ means residual activity present if tested under conditions optimal for the enzyme,
− means no residual activity present if tested under conditions optimal for the enzyme.

Example 9

Activity of the *A. niger* Proline Specific Endoprotease Towards Various Gluten Epitopes A number of publications specify wheat gluten derived peptides that are recognized by small intestinal T-cells from celiac disease patients. In this context peptide binding to HLA-DQ2 molecules is of special interest because persons carrying only the HLA-DQ2 haplotype have by far the highest chance of developing celiac disease (Maki et al.; N Engl J Med. 2003 Jun. 19; 348(25):2517-24). All adult HLA-DQ2 patients examined respond to the alpha-GLIA sequences Glia-alpha2 and Glia-alpha9 (Arentz-Hansen et al, J. Exp. Med. 2000; 6:337-342). Children with recent onset celiac disease respond towards the peptides Glia-alpha20, Glia-gamma30, Glt-17, Glt-156 and Glu-21 (Vader et al, Gastroenterology 2002; 122:1729-1737). In Example 6 we have already demonstrated successful cleavage of the Glia-alpha2 peptide (PQPQLPYPQPQLPY) by the *A. niger* derived enzyme. Here we test whether or not the *A. niger* enzyme can also cleave other relevant wheat gluten derived peptides as well as homologues of these peptides derived from other cereals.

To that end the relevant peptides were synthesized after which their purities were confirmed by rpHPLC and mass spectrometry (MALDI-TOF) according to the procedure described in the Materials & Methods section. Peptide digestions were carried out by mixing 50 microliter of the peptide solution (1 mg/ml) with 50 microliter of the *A. niger* enzyme solution containing 0.43 microgram/ml (0.043 milli units) in 50 millimol/l ammonium acetate buffer pH 4.5. After various incubation periods at room temperature 0.5 microliter samples were taken and added to 9.5 microliter of a matrix solution (1:1$H_2O$ and $CH_3CN$ containing 0.2% TFA). After desalting using Dowex ion resin beads, the liquid was spotted on a MALDI-plate together with some relevant reference peptides after which all peptides were analysed. From the data obtained, cleavage sites as indicated in Table 6 could be deduced. Peptides Glt 156 en Glia gamma-2 are 10-mers; Glt 17 is an 8-mer but requires C-terminale extension by a P and an L residue for optimal binding. Unequivocal cleavage sites are indicated by double vertical lines, cleavage sites that were less evident are indicated by a single vertical line. The known minimal T-cell epitopes on each peptide are indicated by underlining. The U's used in Glu-5 represent either a leucine or an isoleucine residue.

From the data obtained it is clear that not only Glia-alpha2 but in fact all gluten epitopes relevant for young as well as adult HLA-DQ2 patients are efficiently hydrolysed by the *A. niger* derived proline specific protease. As most of the cleavage sites can be pinpointed to the known minimal T-cell epitope binding sites, it is likely that exposure of the gluten epitopes to the enzyme will abolish recognition and thus effectively prevent subsequent T-cell proliferation that ultimately leads to the symptoms characteristic for celiac disease patients.

TABLE 6

Cleavage sites of the *A. niger* derived endoprotease in various known wheat gluten epitopes.

| | |
|---|---|
| Glia-α2 | PQ//PQLP//YPQPQLPY |
| Glia-α9 | QLQP//FP//QPQLP//Y |
| Glia-α20 | PFRP//QQP//YP/QPQPQ |
| Glia-γ1 | QPQQP//QQSFP//QQQRP//F |
| Glia-γ2 | QQP//YPQQP//QQP FPQ |
| Glia-γ30 | VQGQGIIQP//QQPAQL |
| Glt-17 | QQPP//FSQQQQQP//LP Q |
| Glt-156 | QQPP//FSQQQQSP/FSQ |
| Glu-5 | QQUSQP//QUP//QQQQUP//QQPQQF |
| Glu-21 | QPQP//FP//QQSEQSQQP//FQP QPF |

In Table 6, the sequence identification numbers for the listed sequences beginning with PQPQLPYPQPQLPY through to QPQPFPQQSEQSQQPFQPQPF are SEQ ID NOS: 42 and 44-52, respectively.

In a similar approach cleavage sites of the *A. niger* derived enzyme in a number of oats, barley and rye derived gluten homologues of the wheat gluten epitopes were established (Vader, W et al, Gastroenterology 2003; 125:1105-1113). The results obtained (see Table 7) illustrate that the *A. niger* derived enzyme can not only cleave the wheat gluten epitopes responsible for celiac disease but also homologues of these peptides that are present in oats, barley and rye. As in Table 6, unequivocal cleavage sites are indicated by double lines.

TABLE 7

Cleavage sites of the *A. niger* derived endoprotease in various known non-wheat gluten epitopes

| Gluten source | Reference | Amino acid sequence | Homologue of wheat gluten epitope |
|---|---|---|---|
| Oats | Av-gamma2B | QQP//FVQQQQP//FVQ | Glia-gamma2 |
| Oats | Av-gamma2A | QQP//FVEQQEQPFVQ deamidated | Glia-gamma2 |
| Oats | Av-gamma2B | QQP//FVQQQQP//FVQQ | Glia-gamma2 |
| Barley | Hor-alpha2 | QQFP//QPQQP//FPQQP | Glia-alpha2 |
| Barley | Hor-alpha9 | PQQP//FP//QP//QQPFR//Q | Glia-alpha9 |
| Rye | Sec-alpha2 | QP//FP//QP//QQPFPQSQ | Glia-alpha2 |

In Table 7, the sequence identification numbers for the listed sequences beginning with QQP//FVQQQQP//FVQ through to QP//FP//QP//QQPFPQSQ are SEQ ID NOS: 53-58, respectively.

Example 10

Testing the Recovery of Gluten Epitopes from 100% Malt Beer and 100% Wheat Bread The extraction procedure as conceived (see Materials & Methods section) was tested in combination with the antibody based assay on a PVPP treated 100% malt beer (see Example 11) and on a 100% wheat bread sample (see Example 12). According to the results obtained (see Table 8), the extraction procedure in combination with the antibody assay can detect anti-alpha gliadin, anti-gamma gliadin as well as anti-glutenin epitopes in beer as well as bread.

Taken together, the data obtained strongly suggest that the extraction procedure as applied is suitable for the detection of gluten in both the beer and bread sample. Based on these results beer and bread samples subjected to different concentrations of the *A. niger* derived proline specific endoprotease during their processing were more closely examined in Examples 11 and 12.

TABLE 8

Results of the antibody assay. Two dilutions of the samples were measured: 1/16 and 1/64. The results are expressed as ug/ml of the original sample.

| Sample dilution | Anti-alpha gliadin | | Anti-gamma gliadin | | Anti-glutenin | |
|---|---|---|---|---|---|---|
| | 1/16 | 1/64 | 1/16 | 1/64 | 1/16 | 1/64 |
| Beer | >> | 2497 | 1063 | 786 | 166 | 163 |
| Bread | >> | 1050 | 1738 | 1536 | 404 | 215 |

Example 11

Beer Production involving the Proline Specific Endoprotease from *A. niger* Leads to Lower Levels of Gluten Epitopes Beer haze is formed by the association of gluten derived proline rich proteins, polypeptides and peptides with polyphenols that are extracted from the cereals (mostly barley) used for beer production. As described in WO 02/046381 the formation of beer haze can be reduced or prevented by incorporating an acid stable proline specific endoprotease during either the mashing, fermentation or lagering phase of beer production. In the conventional beer brewing process haze formation is prevented by a treatment with PVPP, a compound that binds the various polyphenols present but with only a minor effect on the level of haze active, proline rich peptides. Because the conventional brewing process does not eliminate the toxic proline rich peptides, celiac patients are not allowed to drink beer.

The purpose of the present study is to establish if addition of the *A. niger* derived proline specific endoprotease during the beer making process will result in lowered levels of toxic proline rich peptides in the final beer. If so such beers could be drunk by celiac patients.

Beer production was carried out in a 20 hl pilot plant at IFBM (Nancy, France). The *A. niger* derived proline specific endoprotease sample used was stabilised in 50% glycerol (w/w) and had a final activity of 5 units/gram liquid (see Materials & Methods section for the unit definition).

In independent production runs, five 100% malt beers were brewed by using either PVPP (reference) or different quantities of the proline specific endoprotease to prevent haze formation. In all experiments the mashing protocol used was exactly the same. Depending on the experiment, the proline specific protease was added either at the beginning of the mashing process or after the mashing process just before the beer fermentation. In the mashing process three different enzyme dosages were tested, i.e. 2.5, 5.0 and 7.5 enzyme units per kg malt used. In fermentation only a single enzyme dosage was tested, i.e. 0.75 enzyme units per kg malt added. The reference beer was stabilised with 30 grams/hi PVPP added before the beer filtration.

Each brew was produced from 300 kg of barley malt and hop pellets. Mashing conditions of liquid/grist of 3:1 (vol/wt) and pH 5.6 were used. The mashing diagram includes a first step at 45° C. for 20 minutes, a second step at 64° C. for 15 min and a third step at 76° C. for 25 min and finally a heating to 78° C. Between the steps the heating rate is 1° C. per min. The wort was boiled 90 min. Good trub separations were performed on a Whirlpool. The fermentation was carried out with a bottom yeast strain at the pitching rate of 17 $10^6$ cells/ml of wort and viability at pitching of about 97%. The fermentation period of 10 days at 12° C.+/−1° C. was followed by a cold maturation of 5 days at −1° C.+/−1° C. The beer were carbonated at a pressure of 5.2 g/l and, after bottling, pasteurised at 60° C. for 20 min.

TABLE 9

Different beers and their gluten levels as determined in antibody assays.

| | Beer stabilisation method | | | | |
|---|---|---|---|---|---|
| | Beer 1 | Beer 2 fermentation | Beer 3 mashing | Beer 4 mashing | Beer 5 mashing |
| PVPP | 30 g/hl | | | | |
| Enzyme units/kg malt used | | 0.75 | 2.5 | 5.0 | 7.5 |
| Antibody assays (microgram/ml) | | | | | |
| Anti-alpha gliadin | | | | | |
| Dilution 1/16 | 713 | 15 | 553 | 327 | 199 |
| Dilution 1/64 | 225 | 2 | 163 | 78 | 71 |
| Anti-gamma gliadin | | | | | |
| Dilution 1/16 | 114 | 8 | 74 | 87 | 42 |
| Dilution 1/64 | 45 | 3 | 26 | 20 | 22 |
| Anti-glutenin | | | | | |
| Dilution 1/16 | 14 | 4 | 9 | 6 | 8 |
| Dilution 1/64 | 21 | 3 | 13 | 4 | 10 |

According to the results the anti-alpha gliadin and anti-gamma gliadin antibodies yield comparable data. The results with the anti-glutenin antibody in this assay are non-conclusive. Evident is that especially application of the enzyme after the mashing stage leads to very low levels of toxic proline rich peptides in the beer. The consideration that antibody recognition sites have a minimal length of 5 amino acid residues but a T-cell recognition site requires at least 9 amino acid residues, makes it even more unlikely that T-cells can recognize the short peptides generated in the fermentation approach. In fact these data strongly indicate that following the above mentioned enzyme approach beers can be brewed that are safe for celiac patients.

Example 11

Bread Produced by Incorporating the Proline Specific Endoprotease from *A. niger* into the Dough Results in Lower Levels of Gluten Epitopes For bread making a dough was prepared from 3500 g of wheat flour (80% Kolibri™ and 20% Ibis™), 1990 ml water (56%), 77 g compressed yeast (2.2%), 70 g salt (2%), 140 mg ascorbic acid (40 ppm) and various quantities of the *A. niger* derived enzyme as indicated in Table 10. Quantities of enzymes added were compensated by adding less water to the dough.

The ingredients were mixed into a dough using a Diosnar® spiral mixer for 2 minutes at speed 1 followed by 6 minutes mixing at speed 2. Dough pieces of 875 g were rounded, proofed for 35 minutes at 34° C. and 85% RH, punched, moulded, panned, proofed for 75 minutes at 38° C. and 87% RH and baked for 20 minutes at 220° C. The evaluation of doughs and final bread was carried out by a professional baker. From the results in Table 10 it is clear that addition of the proline-specific endoprotease apparently did not affect the gluten network and gas-retaining capacity of the dough because the loaf volumes and firmness values were not affected by enzyme concentrations of 225 units per kg flour or lower. In fact only the addition of higher enzyme dosages imparts negative effects on the dough and generates loafs which would be considered unacceptable by most consumers. Because of the latter observation, antibody assay data for breads produced with the highest enzyme concentration were not generated. The data depicted in Table 10 show a clear decrease of the toxic proline rich peptides present in breads produced with an enzyme concentration around 200 units per kg flour. Very likely this decrease will proof to be insufficient to allow consumption of such breads by celiac patients. However, the decrease could be large enough to prepare foods with prophylactic benefits for people suffering from an unnoticed celiac disease or from IBS or even for infants with an immature immune system.

TABLE 10

Different 100% wheat breads and their gluten levels as determined in antibody assays.

| | Enzyme units/kg flour used | | | |
|---|---|---|---|---|
| dosage | 0 | 45 | 225 | 450 |
| dough consistency | good | good | acceptable | unacceptable |
| dough extensibility | good | good | high | very high |
| loaf volume | good | large | large | small |
| loaf structure | good | good | good | very coarse crumb structure |
| Antibody assays (microgram/ml) | | | | |
| Anti-alpha gliadin | | | | |
| Dilution 1/16 | 4231 | 4231 | 237 | not |
| Dilution 1/64 | 2347 | 2212 | 124 | determined |
| Anti-gamma gliadin | | | | |
| Dilution 1/16 | 1926 | 1509 | 1183 | not |
| Dilution 1/64 | 3979 | 2895 | 888 | determined |
| Anti-glutenin | | | | |
| Dilution 1/16 | 359 | 74 | 98 | not |
| Dilution 1/64 | 232 | 232 | 121 | determined |

The invention claimed is:

1. A method of using a proline specific endoprotease to hydrolyse at a pH of below 5.5, proline rich peptides which are brought with celiac disease, a disease associated with the occurrence of celiac disease, or a disease caused by a decreased level in a patient's body of proline specific proteases required for breakdown of these peptides, the method comprising administering a dietary supplement or a medicament comprised of said proline specific endoprotease for ingestion by a patient in need thereof, whereby the proline specific endoprotease is active in the stomach and is pepsin resistant.

2. A method of using a proline specific endoprotease having a pH optimum below 6.5, the method comprising administering said proline specific endoprotease for ingestion by a patient in need thereof, whereby the patient suffers from celiac disease, a disease associated with the occurrence of celiac disease, or a disease caused by a decreased level in the patient's body of proline specific proteases, and whereby the proline specific endoprotease is active in the stomach and is pepsin resistant.

3. The method according to claim 2, wherein the proline specific endoprotease is an *Aspergillus* enzyme.

4. The method according to claim 1, wherein the proline specific endoprotease is an *Aspergillus* enzyme.

5. The method according to claim 1, wherein the proline specific endoprotease is an *Aspergillus niger* enzyme.

6. The method according to claim 2, wherein the proline specific endoprotease is an *Aspergillus niger* enzyme.

7. The method according to claim 1, wherein the patient suffers from celiac disease.

8. The method according to claim 2, wherein the patient suffers from celiac disease.

9. The method according to claim 1, wherein the patient is gluten sensitive.

10. The method according to claim 2, wherein the patient is gluten sensitive.

* * * * *